(12) United States Patent
Ruan

(10) Patent No.: US 9,637,488 B2
(45) Date of Patent: May 2, 2017

(54) HETEROCYCLIC COMPOUNDS AS INHIBITORS OF CLASS I PI3KS

(71) Applicant: Fuqiang Ruan, Bellevue, WA (US)

(72) Inventor: Fuqiang Ruan, Bellevue, WA (US)

(*) Notice: Subject to any disclaimer, the term of this patent is extended or adjusted under 35 U.S.C. 154(b) by 0 days.

(21) Appl. No.: 14/998,635

(22) Filed: Jan. 27, 2016

(65) Prior Publication Data

US 2016/0222012 A1    Aug. 4, 2016

Related U.S. Application Data

(60) Provisional application No. 62/125,731, filed on Jan. 29, 2015.

(51) Int. Cl.
| | | |
|---|---|---|
| *C07D 473/34* | (2006.01) |
| *A61K 31/52* | (2006.01) |
| *A61K 31/5377* | (2006.01) |
| *C07D 401/14* | (2006.01) |
| *A61K 31/506* | (2006.01) |
| *A61K 31/55* | (2006.01) |
| *A61K 45/06* | (2006.01) |

(52) U.S. Cl.
CPC .......... *C07D 473/34* (2013.01); *A61K 31/506* (2013.01); *A61K 31/52* (2013.01); *A61K 31/5377* (2013.01); *A61K 31/55* (2013.01); *A61K 45/06* (2013.01); *C07D 401/14* (2013.01)

(58) Field of Classification Search
None
See application file for complete search history.

(56) References Cited

U.S. PATENT DOCUMENTS

| 8,586,739 | B2* | 11/2013 | Chen | C07D 473/30 |
|---|---|---|---|---|
| | | | | 544/119 |
| 8,785,470 | B2 | 7/2014 | Castro et al. | |
| 8,828,998 | B2 | 9/2014 | Palombella et al. | |
| 8,940,742 | B2 | 1/2015 | Castro et al. | |
| 8,940,752 | B2 | 1/2015 | Li et al. | |
| 2011/0152296 | A1 | 6/2011 | Cushing et al. | |
| 2015/0011569 | A1 | 1/2015 | Katsikis et al. | |

FOREIGN PATENT DOCUMENTS

| WO | WO2005113556 A1 | 12/2005 |
|---|---|---|
| WO | WO2008118454 A2 | 10/2008 |
| WO | WO2008118455 A1 | 10/2008 |
| WO | WO2008118468 A1 | 10/2008 |
| WO | WO2009064802 A2 | 5/2009 |
| WO | WO2009081105 A2 | 7/2009 |
| WO | WO2009081105 A3 | 8/2009 |
| WO | WO2010027097 A1 | 3/2010 |
| WO | WO2011075628 A1 | 6/2011 |
| WO | WO2011123751 A2 | 10/2011 |
| WO | WO2011075630 A1 | 12/2011 |
| WO | WO2012003271 A1 | 1/2012 |
| WO | WO2012087881 A1 | 6/2012 |
| WO | WO2012107465 A1 | 8/2012 |
| WO | WO2012061696 A1 | 10/2012 |
| WO | WO2013052699 A3 | 6/2013 |
| WO | WO2013152150 A1 | 10/2013 |
| WO | WO2014015830 | 1/2014 |
| WO | WO2014100765 A1 | 6/2014 |
| WO | WO2014128612 A1 | 8/2014 |
| WO | WO2014201409 A1 | 12/2014 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*
Al-Alwan, M.M. et al., J. Immunol. (2007) 178:2328-2335.
Alexander, A.G. et al., Lancet. (1992) 339(8789):324-8.
Ali, K. et al., J. Immunol. (2008) 180:2538-2544.
Ali, K. et al., Nature (2004) 431(7011):1007-11.
Ali, K. et al., Nature (2014) 510(7505):407-11.
Azijli K. et al., Anticancer Research (2014) 34(4):1493-1505.
Bean, G.R. et al., Sci. Signal. (2013) 6:ra20.
Berge, S.M. et al., J. Pharm. Sci. (1977) 66:1-19.
Bilancio, A. et al., Blood (2006) 107:642-650.
Burger, J.A. Curr. Opin. Oncol. (2012) 24(6):643-649.
Carayol, N. et al., Proc. Natl Acad. Sci. USA (2010) 107:12469-12474.
Chakrabarty, A. et al., Cancer Res. (2013) 73:1190-1200.
Coffee, E.M. et al., Clin. Cancer Res. (2013) 19:2688-2698.
Coloff, J.L. et al., Cancer Res. (2011) 71: 5204-5213.
Cushing. T.D. et al., J Med Chem. (2015) 58(1):480-511.
Davids, M.S. et al., Blood (2012) 120:3501-3509.
Dawson, M.A. et al., Nature (2011) 478:529-533.
Delmore, J.E. et al., Cell (2011) 146: 904-917.
Di Paolo, G. et al., Nature (2006) 443:651-657.
Dominguez-Sola, D. et al., Cancer Cell (2012) 22:141-142.
Donev, I.S. et al., Clin. Cancer Res. (2011) 17:2260-2269.
Eickholk, B.J. et al., PLoS One (2007) 2(9):e869.
Eliel, E. and Wilen, S., Stereochemistry of Organic Compounds (1994) John Wiley & Sons, Inc., New York.
Ellenrieder, V. et al., Cancer Res. (2001) 61:4222-4228.
Engelman J.A. et al., Nat Rev Genet. (2006) 7(8):606-19.
Engelman, J.A. et al. Nature Med. (2008) 14:1351-1356.
Fan, Q.W. et al., Sci. Signal. (2010) 3:ra81.
Fiskus, W. et al., Mol. Cancer Ther. (2013) 12:577-588.
Floris, G. et al., Clin. Cancer Res. (2013) 19:620-630.
Francois-Xavier et al., J. Org. Chem. (2001) 66(19):6305-6312.
Foster, A.B., Trends Pharmacol. Sci. (1984) 5:524-527.
Fruman D.A. et al. Cancer Discovery ( 2011) 1(7):562-572.
Fruman, D.A. et al., Nat Rev Drug Discov. (2014) 13(2):140-56.
Garcia-Echeverria, C. et al., Oncogene (2008) 27(41):5511-26.
Ghigo, A. et al., Future Med Chem. (2013) 5(4):479-92.
Greene T.W. et al., Protective Groups in Organic Synthesis, 3rd edition (1999) John Wiley & Sons.
Haynes, D.A. et al., J. Pharm. Sci. (2005) 94:2111-2120.
Higuchi et al., Pro-drugs as Novel Delivery Systems, vol. 14 of the A.C.S. Symposium Series.
Hiles, I.D. et al., Cell (1992) 70(3):419-29.
Hsieh, A.C. et al., Nature (2012) 485:55-61.

(Continued)

*Primary Examiner* — Dennis Heyer

(57) ABSTRACT

The present application discloses a novel class of heterocycles as class I PI3Ks inhibitors. The compounds claimed herein could be used alone or in combination therapies for the treatment of a wide range of disorders such as autoimmune, inflammatory and allergic diseases, asthma, COPD, parasitic infections, diabetes, and cancer.

4 Claims, No Drawings

(56) References Cited

OTHER PUBLICATIONS

Ibrahim, Y.H. et al., Cancer Discov. (2012) 2:1036-1047.
IMPAKT 2015 News: PI3 Kinase and CDK4/6 Inhibitors Are Highly Active in ER-Positive Breast Cancer.
Juvekar, A. et al., Cancer Discov. (2012) 2:1048-1063.
Kao, G.D. et al., J. Biol. Chem. (2007) 282:21206-21212.
Keng, M.K. et al., Curr Hematol Malig Rep. (2013) 8(3):226-35.
Kok, K. et al., Trends Biochem Sci. (2009) 34(3):115-27.
Kumar, A. et al., Proc. Natl Acad. Sci. USA (2010) 107:7491-7496.
Lau, C. et al., J. Immunol. (2008) 180:870-880.
Lee, K.S. et al., J Allergy Clin Immunol. (2006) 118(2):403-9.
Liu et al., Nat Rev Drug Discov. (2009) 8(8):627-44.
Liu, Y. et al., Mol. Cancer Ther. (2012) 11:45-56.
Lizcano, JM et al., Curr. Biol. (2002) 12:236-238.
March's Advanced Organic Chemistry (Michael B. Smith & Jerry March, Wiley-Interscience (2000).
Markham, A. Drugs (2014) 74:1701-1707.
Marwick, J.A. et al., Am. J. Respir. Crit. Care Med. (2009) 179(7):542-8.
Mertz, J.A. et al., Proc. Natl Acad. Sci. USA (2011) 108:16669-16674.
Miller, T.W. et al., J. Clin. Oncol. (2011) 29:4452-4461.
Modern Pharmaceutics, Marcel Dekker, Inc. 3rd Ed. (G.S. Banker & C.T. Rhodes, Eds.).
Mulholland, D.J. et al., Cancer Res. (2012) 72:1878-1889.
Munck, J.M. et al., Mol. Cancer Ther. (2012) 11:1789-1798.
Otsu, M. et al., Cell (1991) 65(1):91-104.
Paquette, L.A., Principles of Modern Heterocyclic Chemistry (W. A. Benjamin, New York, 1968), particularly Chapters 1, 3, 4, 6, 7, and 9.
Parker, Biochemical Society Transactions (2004) 32(6):893-898.
Parker S.P., Ed., McGraw-Hill Dictionary of Chemical Terms (1984) McGraw-Hill Book Company, New York.
Posch, C. et al., Proc. Natl Acad. Sci. USA (2013) 110:4015-4020.
Pourdehnad, M. et al., Proc. Natl Acad. Sci. USA (2013) 110:11988-11993.
Puri, K.D. et al., Blood (2004) 103(9):3448-56.
Rahmani, M. et al., Cancer Res. (2013) 73:1340-1351.
Remington's Pharmaceutical Sciences, 18th Ed., Mack Publishing Co, Easton PA., 1990.
Rexer, B.N. & Arteaga, C.L., Cancer Res. (2013) 73:3817-3820.
Roche (ed.), Bioreversible Carriers in Drug Design, American Pharmaceutical Association and Pergamon Press (1987), Chapter 1, pp. 1-12.
Sander, S. et al., Cancer Cell (2012) 22:167-179.
Schaeffer, E.M. et. al., Curr. Opin. Immunol. (2000) 12:282-288.
Schmitz, R. et al., Nature (2012) 490:116-120.
Shanware, N.P. et al., Annu. Rev. Pharmacol. Toxicol. (2013) 53:89-106.
Shimizu, T. et al., Clin. Cancer Res. (2012) 18:2316-2325.
The Chemistry of Heterocyclic Compounds, A series of Monographs (John Wiley & Sons, New York, 1950 to present).
The Practice of Medicinal Chemistry (Camile G. Wermuth, Academia Press, 2003).
Tobrman, T. et al, Synthesis (2014) 46(05):660-668.
Vora, S.R. et al., Cancer Cell (2014) 26:136-149.
Wander, S.A. et al., J Clin Invest. (2011) 121(4):1231-41.
Wang, J. et al., Chin. J. Chem. (2012) 30(12):2813-2818.
Workman, P. et al., Cancer Res. (2010) 70:2146-2157.
Young, C.D. et al., Cancer Res. (2013) 73:4075-4085.
Zuber, J. et al., Nature (2011) 478:524-528.

* cited by examiner

HETEROCYCLIC COMPOUNDS AS INHIBITORS OF CLASS I PI3KS

CROSS-REFERENCE TO RELATED APPLICATION

This application claims the benefit of priority to U.S. provisional patent application Ser. No. 62/125,731, filed Jan. 29, 2015, which is hereby incorporated by reference.

FIELD OF THE INVENTION

The present invention relates generally to phosphatidylinositol 3-kinases (PI3Ks), and more specifically to novel selective inhibitors of class I PI3Ks and methods of making and using such inhibitors.

BACKGROUND OF THE INVENTION

The signaling network defined by phosphoinositide 3-kinases (PI3Ks), the serine/threonine kinases AKT (or PKB) and mammalian target of rapamycin (mTOR) is involved in many essential cellular functions including cell growth, proliferation, differentiation, motility, survival, and intracellular trafficking (*Nat. Rev. Genet.* 2006, 7, 606-619; *Nat. Rev. Drug Discov.* 2009, 8, 627-644). To date, eight mammalian PI3Ks have been identified, which can be divided into three classes (class I, II, and III) based on their primary structure, regulatory subunits, and in vitro lipid substrate specificity. The main PI3-kinase isoform in cancer is class I PI3Ks, and the class I PI3Ks are most extensively studied.

Activated by receptor tyrosine kinases and G protein-coupled receptors (GPCRs), class I PI3Ks utilize ATP to phosphorylate the 3-OH of the inositol ring moiety, converting phosphatidylinositol 4,5-bisphosphate (PIP2) to phosphatidylinositol 3,4,5-trisphosphate (PIP3) (*Biochem. Soc. Trans.* 2004, 32, 893-898), a potent secondary messenger that results in the activation of several downstream effectors, including AKT. Dysfunctional regulation of the various phosphoinositides has been implicated in a variety of diseases including cancer, autoimmune disorders, and inflammation (*Nature* 2006, 443, 651-657; *Curr. Opin. Immunol.* 2000, 12, 282-288). Thus, class I PI3Ks are attractive targets for drug discovery and development, and inhibitors of class I PI3Ks could be useful to treat a wide range of disorders such as autoimmune, inflammatory and allergic diseases, asthma, COPD, parasitic infections, diabetes and cancer (see: e.g., *J. Immunol.* 2007, 178, 2328-2335; *Blood* 2006, 107, 642-650; *Blood* 2004, 103, 3448; *J. Allergy Clin. Immunol.* 2006, 118, 403; *Lancet.* 1992, 339, 324; *Nature* 2004, 431, 1007; *J. Immunol.* 2008, 180, 2538; *J. Immunol.* 2008, 180, 870; *Am. J. Respir. Crit. Care Med.* 2009, 179, 542; *Future Med. Chem.* 2013, 5, 479; *Curr. Biol.* 2002, 12, 236).

The initial purification and molecular cloning of PI3Ks revealed that it was a heterodimer consisting of p85 and p110 subunits (*Cell* 1991, 65, 91-104; *Cell* 1992, 70, 419-29). Since then, four distinct class I PI3Ks have been identified, designated PI3K α, β, δ, and γ, each comprising a 110 kDa catalytic subunit and a smaller associated regulatory subunit. Class Ia PI3Ks (α, β, and δ) containing the catalytic subunits p110α, p110β, and p110δ, respectively, are activated through tyrosine kinase signaling. In contrast, the sole class Ib member, PI3Kγ, contains catalytic subunit p110γ associated with either a p101 or p84 regulatory subunit, and is mostly activated through GPCRs. While PI3Kα and PI3Kβ are ubiquitously expressed, PI3Kδ and PI3Kγ are found in leukocytes (B and T cells, and myeloid lineage cells) with PI3Kδ nearly confined to spleen, thymus, and peripheral blood leukocytes (*PLoS One* 2007, 2(9), e869; *Trends Biochem. Sci.* 2009, 34, 115). The dysregulation of PI3Kα and PI3Kβ is implicated in the etiology of solid tumors, and the dysregulation of PI3Kδ and PI3Kγ has been implicated in diseases of the innate and adaptive immune system such as rheumatoid arthritis (RA), systemic lupus erythematosus (SLE), and hematological malignancies. Thus selective inhibitors of PI3Kδ and/or dual PI3Kδ/PI3Kγ could provide promising therapeutic benefits to a wide variety of patients.

The central role of PI3Ks activation in tumour cell biology has prompted quite extensive drug hunting efforts, which has led to the discovery of compounds targeting PI3Ks, including downstream kinases such as AKT and mammalian target of rapamycin (mTOR) in cancer (e.g., *Oncogene* 2008, 27, 5511-5526; *J. Clin. Invest.* 2011, 121, 1231-1241; *Cancer Res.* 2010, 70, 2146-2157; *J. Med. Chem.* 2015, 58, 480; WO2005/113556; WO2008/118468; U.S. Pat. No. 8,828,998B2); however, challenges remain, and emerging clinical data show limited single-agent activity of inhibitors targeting PI3K, AKT or mTOR at tolerated doses (*Nat. Rev. Drug Discov.* 2014, 13, 140). One exception is the response to PI3Kδ inhibitors in chronic lymphocytic leukaemia, where a combination of cell-intrinsic and -extrinsic activities drive efficacy. The p110δ-selective inhibitor GS-1101 (formerly known as CAL-101, and currently trade name as Zydelig approved on Jul. 23, 2014 by the U.S. Food and Drug Administration) produces dramatic responses in some B cell malignancies in combination with the anti-CD20 mAB rituximab (*Drugs* 2014, 74, 1701). This proves the principle that a potent and selective PI3K inhibitor can improve the survival of selected patient populations in cancer. However, GS-1101 has an unusual mechanism of action: the drug is not directly cytotoxic to malignant B lymphoma cells and its efficacy arises in part from modulating the immune environment of the tumour (*Cancer Discov.* 2011, 1, 562-572; *Curr. Hematol. Malignancy Rep.* 2013, 8, 22-27; *Curr. Opin. Oncol.* 2012, 24, 643-649). Recent preclinical studies further indicated that p110δ inactivation in mice protects against a broad range of cancers, including non-haematological solid tumours (*Nature* 2014, 510, 407). Thus, there exists a need for novel selective inhibitors of class I PI3Ks. A novel PI3Kδ inhibitor could be used to understand the biology of the PI3K pathway in immune cells and in physiological models of tumour immunity (or immunology), and a novel PI3Kδ and/or a dual PI3Kδ/PI3Kγ inhibitor could have the potential therapeutic usefulness in immuno-oncology.

In addition, abundant evidence from genomic analysis has revealed that PI3K pathway is the most frequently mutated or altered pathway via PIK3CA (phosphatidylinositol-4,5-bisphosphate 3-kinase, catalytic subunit alpha) and PTEN (phosphatase and tensin homologin) in numerous forms of human cancers. Thus, a novel therapeutically effective inhibitor of PI3Ks is a promising therapeutic option, in association with known systemic cytotoxic and biological therapeutics, including immune checkpoint inhibitors, to overcome the often-rapid onset of resistance in responsive cancer patients based on emerging rational combination strategies, appropriate biomarkers and patient-specific mutation profiles (see: e.g., *Nat. Rev. Drug Discov.* 2014, 13, 140; *Anticancer Research* 2014, 34, 1493). Furthermore, a novel PI3K inhibitor, preferably with certain isoform selectivity patterns to minimize off-target effects, could be used to treat and prevent indications mediated by class I PI3Ks including inflammatory conditions, autoimmune conditions and angiogenesis. The present invention provides such compounds as further described below.

SUMMARY OF THE INVENTION

The present invention provides the compounds of the formula (I):

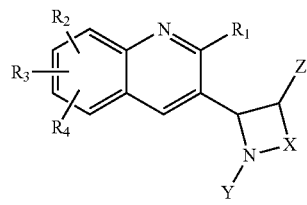

(I)

or stereoisomers, geometric isomers, tautomers, solvates (e.g., hydrate), metabolites, prodrugs, isotopically-labeled derivates, and pharmaceutically acceptable salts thereof, wherein:

X is selected from: —$CHZ^1$—, —$CHZ^1CHZ^2$—, —$CHZ^1CHZ^2CHZ^3$—, —$CHZ^1CHZ^2CHZ^3CHZ^4$—, —$CZ^1$=$CZ^2$—, —$CHZ^1CZ^2$=$CZ^3$—, —$CHZ^1CZ^2$=$CZ^3CHZ^4$—. Z, $Z^1$, $Z^2$, $Z^3$, and $Z^4$ are optionally selected from a group of hydrogen, deuterium, halogen, $C_1$-$C_6$ alkyl, $C_1$-$C_6$ haloalkyl, $C_1$-$C_6$ hydroxyalkyl, —OH, $C_1$-$C_8$ alkoxyalkyl, $C_1$-$C_8$ alkoxy;

In one preferred embodiment, X is selected from: —$CHZ^1CHZ^2$—, —$CHZ^1CHZ^2CHZ^3$—, —$CHZ^1CZ^2$=$CZ^3$—. Z, $Z^1$, $Z^2$, and $Z^3$ are as defined above;

$R_1$ is selected from: a carbon-bond or nitrogen-bond of an unsubstituted or substituted aryl, heteroaryl, cycloalkyl, heterocycloalkyl, or —NH-heteroaryl, or —NH—$C_1$-$C_4$ alkyl-cycloalkyl, or —NH—$C_1$-$C_4$ alkyl-heterocycloalkyl, or —N($C_1$-$C_6$ alkyl)$C_2$-$C_6$ alkyl-$OR^a$, or —N($C_1$-$C_6$ alkyl) $C_2$-$C_6$ alkyl-$NR^aR^a$, wherein $R^a$ is independently selected from: hydrogen, $C_1$-$C_6$ alkyl, $C_1$-$C_6$ hydroxyalkyl, benzyl, or phenyl being substituted by 0, 1, 2, or 3 substituents selected from a group of halogen, $C_1$-$C_4$ alkyl, $C_1$-$C_3$ haloalkyl, —$OC_1$-$C_6$ alkyl, —$NH_2$, —$NHC_1$-$C_4$ alkyl, —$N(C_1$-$C_6$ alkyl)$C_1$-$C_6$ alkyl;

In one embodiment, $R_1$ is phenyl, 5- and 6-membered heteroaryl containing 1, or 2 atoms selected from N, O, S, but containing no more than one O or S; wherein the available carbon atoms of the ring is unsubstituted or substituted by one or two substituents, independently selected from: hydrogen, deuterium, halogen, cyano, nitro, $C_1$-$C_6$ alkyl, $C_2$-$C_6$ alkenyl, $C_2$-$C_6$ alkynyl, —$OC_1$-$C_6$ alkyl, —$OC_2$-$C_6$ alkyl $NR^aR^a$, —$OC_2$-$C_6$ alkyl $OR^a$, —$N(C_1$-$C_6$ alkyl)$C_1$-$C_6$ alkyl, $C_1$-$C_6$ haloalkyl, $C_1$-$C_6$ hydroxyalkyl, $C_1$-$C_8$ alkoxyalkyl, $C_1$-$C_8$ alkoxy, —C(=O)$R^a$, —C(=O) $OR^a$, —C(=O)$NR^aR^a$, —C(=$NR^a$)$NR^aR^a$, —$OR^a$, —OC (=O)$R^a$, —OC(=O)$OR^a$, —OC(=O)$NR^aR^a$, —$NR^aC$ (=O)$R^a$, —$NR^aC$(=O)$OR^a$, —$NR^aC$(=O)$NR^aR^a$, —$SR^a$, —S(=O)$R^a$, —S(=O)$_2R^a$, —S(=O)$_2NR^aR^a$, —$NR^aS$ (=O)$_2R^a$, —$NR^aS$(=O)$_2NR^aR^a$;

In one embodiment, $R_1$ is a carbon-bond, or nitrogen-bond, or —$NHC_1$-$C_3$ alkyl linked, 3- to 7-membered monocyclic ring containing 0, 1, or 2 atoms selected from N, O, S, but containing no more than one O or S, wherein the available carbon atoms of the ring is unsubstituted or substituted by one or two substituents, independently selected from: 0, or 1 oxo or thioxo group, hydrogen, deuterium, halogen, cyano, nitro, $C_1$-$C_6$ alkyl, $C_2$-$C_6$ alkenyl, $C_2$-$C_6$ alkynyl, $OC_1$-$C_6$ alkyl, —$OC_2$-$C_6$ alkyl $NR^aR^a$, —$OC_2$-$C_6$ alkyl $OR^a$, —$N(C_1$-$C_6$ alkyl)$C_1$-$C_6$ alkyl, $C_1$-$C_6$ haloalkyl, $C_1$-$C_6$ hydroxyalkyl, $C_1$-$C_8$ alkoxyalkyl, $C_1$-$C_8$ alkoxy, —C(=O)$R^a$, —C(=O)$OR^a$, —C(=O)$NR^aR^a$, —C(=$NR^a$)$NR^aR^a$, —$OR^a$, —OC(=O)$R^a$, —OC(=O) $OR^a$, —OC(=O)$NR^aR^a$, —$NR^aC$(=O)$R^a$, —$NR^aC$(=O) $OR^a$, —$NR^aC$(=O)$NR^aR^a$, —$SR^a$, —S(=O)$R^a$, —S(=O)$_2$ $R^a$, —S(=O)$_2NR^aR^a$, —$NR^aS$(=O)$_2R^a$, —$NR^aS$(=O)$_2NR^aR^a$;

$R_2$, $R_3$, $R_4$ are independently selected from: hydrogen, deuterium, $C_1$-$C_6$ alkyl, difluoromethyl, trifluoromethyl, trideuteromethyl, methoxy, difluoromethoxy, trifluoromethoxy, hydroxy, cyano, halogen, $C_1$-$C_6$ alkylamino, 5- or 6-membered heteroaryl, or —NH-linked heteroaryl, or $R_2$ and $R_3$ or $R_4$ are taken together to form a 5- to 7-membered ring, optionally containing at least one heteroatom selected from the group consisting of N, O, and S;

Y is selected from an optionally substituted mono- or bicyclic heteroaryl group containing at least one nitrogen atom. In a preferred embodiment, Y is selected from:

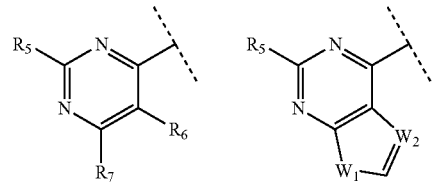

wherein:

$R_5$ is independently selected from —H, —$NH_2$, —CN, —$CONH_2$, halogen;

$R_6$ is independently selected from: —H, —$CH_3$, —CN, trifluoromethyl, difluoromethyl, trideuteromethyl, amino, or an unsubstituted or substituted 5- to 6-membered heteroaryl, or -ethynylheteroaryl;

$R_7$ is selected from: —H, —$NH_2$;

$W_1$ is independently selected from NH, $NCH_3$ or S;

$W_2$ is independently selected from N, C—H, C-D, C—F, or C—$CH_3$.

In some embodiments, the compounds are the atropisomers. In other embodiments, the compounds are the (S)-enantiomer. In some other embodiments, the compounds are the (R)-enantiomer.

Another aspect of the present invention is to provide the compounds of the formula (II):

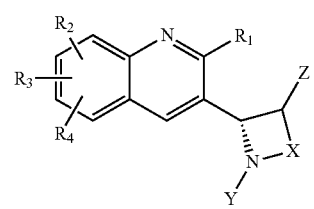

(II)

or stereoisomers, geometric isomers, tautomers, solvates (e.g., hydrate), metabolites, prodrugs, isotopically-labeled derivates, and pharmaceutically acceptable salts thereof, wherein $R_1$, $R_2$, $R_3$, $R_4$, X, Y and Z are as defined above.

Another aspect of the present invention is to provide compounds that inhibit class I PI3Ks, and/or preferably inhibit PI3Kδ and/or PI3Kγ selectively compared to the other PI3K isoforms. This invention identifies potent compounds selectively modulating human class I PI3Ks' activity, and thereby that are useful for medical treatment of diseases mediated by human PI3Kδ and/or PI3Kγ dysfunction, including, but not limit to, proliferative diseases such as cancer and/or relapsed cancer after treatment with chemotherapy. It is preferred that the PI3Kδ inhibitor is selective. It is preferred that the PI3Kδ inhibitor is at least about 100-fold selective for inhibition of p110δ relative to p110α, at least about 40-fold selective relative to p110β, and at least about 10-fold selective relative to p110γ in a biochemical assay. It is preferred that the dual PI3Kδ/PI3Kγ inhibitor is at least about 100-fold selective for inhibition of p110δ and p110γ relative to p110α, at least about 40-fold selective relative to p110β in a biochemical assay. Preferred compounds of the present invention possess an $IC_{50}$ value for the inhibition of PI3Kδ and/or PI3Kγ of less than 10 μM, preferably less than 1 even more preferably less than 0.1 μM, most preferably less than 0.05 μM. Many of the compounds of this invention display unexpected improvements in potency and selectivity for the PI3Kδ and/or PI3Kγ. The compounds are readily synthesized and can be administered to patients by a variety of methods.

Compounds of formula (I) and (II) may contain chiral centers and therefore may exist in different enantiomeric and diastereomeric forms. This invention relates to all optical isomers and all stereoisomers of compounds of the formula (I) and (II), both as racemic mixtures and as individual enantiomers and diastereoismers of such compounds, and mixtures thereof, and to all pharmaceutical compositions and methods of treatment defined below that contain or employ them, respectively.

As the compounds of formula (I) and (II) of this invention may possess at least two asymmetric centers, they are capable of occurring in various stereoisomeric forms or configurations. Hence, the compounds can exist in separated (+)- and (−)-optically active forms, as well as mixtures thereof. The present invention includes all such forms within its scope. Individual isomers can be obtained by known methods, such as optical resolution, optically selective reaction, or chromatographic separation in the preparation of the final product or its intermediate.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The term "stereoisomers" refers to compounds which have identical chemical constitution, but differ with regard to the arrangement of the atoms or groups in space. "Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography. "Enantiomers" refer to two stereoisomers of a compound which are non-superimposable mirror images of one another.

The compounds of the present invention can exist in unsolvated forms as well as solvated forms, including hydrated forms. In general, the solvated forms, including hydrated forms, are equivalent to unsolvated forms and are intended to be encompassed within the scope of the present invention. A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

A "metabolite" is a product produced through metabolism in the body of a specified compound or salt thereof. Metabolites of a compound may be identified using routine techniques known in the art and their activities determined using tests such as those described herein. Such products may result e.g. from the oxidation, reduction, hydrolysis, amidation, deamidation, esterification, deesterification, enzymatic cleavage, and the like, of the administered compound. Accordingly, the present invention includes metabolites of compounds of the invention, including compounds produced by a process comprising contacting a compound of this invention with a mammal for a period of time sufficient to yield a metabolic product thereof.

The present invention also includes isotopically labeled compounds, which are identical to those recited in formula (I) and (II), but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{38}S$, $^{18}F$, and $^{36}Cl$, respectively. Compounds according to formula (I) and (II) described herein or pharmaceutically acceptable salts, tautomers, isomers, prodrugs, or solvates of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. In addition, it is known that the deuterium atom ($^2H$) is a non-radioactive isotope of the hydrogen atom. Such compounds may increase resistance to metabolism, and thus may be useful for increasing the half-life of the compounds of formula (I) and (II) or pharmaceutically acceptable salts, isomers, prodrugs, or solvates thereof, when administered to a mammal (see: e.g., *Trends Pharmacol. Sci.* 1984, 5(12), 524-527). Isotopically labeled compounds of formula (I) and (II) of this invention can generally be prepared by carrying out the procedures disclosed in the Examples of Preparations below, by substituting a readily available isotopically labeled reagent for a non-isotopically labeled reagent.

The terms "compound of this invention", and "compounds of the present invention" and "compounds of formula (I) and/or (II)" include compounds of formulas (I) and (II) and stereoisomers, geometric isomers, tautomers, solvates, metabolites, isotopically labeled derivates, pharmaceutically acceptable salts and prodrugs thereof.

The compounds of formula (I) and (II) are capable of further forming pharmaceutically acceptable formulations comprising salts, including but not limited to acid addition and/or base salts, solvents and N-oxides of a compound of formula (I) and (II).

This invention also provides pharmaceutical formulations comprising a therapeutically effective amount of a compound of formula (I) and (II) or a therapeutically acceptable salt thereof and a pharmaceutically acceptable carrier, diluent, or excipient therefor. All of these forms are within the present invention.

As used herein, the term "alkyl" in the present invention is defined as linear or branched hydrocarbon groups containing the indicated number of carbon atoms and includes, for example, methyl, ethyl, n-propyl, isopropyl, n-butyl, sec-butyl, isobutyl, tert-butyl, n-pentyl, iso-pentyl, n-hexyl, and the like.

By "Alkenyl" in the present invention means a linear or branched hydrocarbon group having the indicated number of carbon atoms and at least one double bond.

By "Alkynyl" in the present invention means a linear or branched hydrocarbon group having from the indicated number of carbon atoms and at least one triple bond.

The term "cycloalkyl" refers to a monovalent non-aromatic, saturated or partially unsaturated ring having 3 to 7 carbon atoms as a monocyclic ring or 7 to 12 carbon atoms as a bicyclic ring. Bicyclic ring having 7 to 12 atoms can be arranged, e.g., as a bicyclo[4,5], [5,5], [5,6] or [6,6] system, and bicyclic ring having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic ring include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, and the like.

By "Aryl" means an aromatic carbocyclic group having a single ring (e.g., phenyl), multiple rings (e.g., biphenyl), or multiple condensed rings in which at least one is aromatic. Aryl groups are optionally substituted independently with one or more substituents described herein.

The terms "heterocycloalkyl", or "heterocyclic ring" are used interchangeably herein and similarly as cycloalkyl except the ring contains one or more heteroatoms selected from nitrogen, oxygen, phosphorus and sulfur, the remaining ring atoms being C, where one or more ring atoms is optionally substituted independently with one or more substituents described herein. A heterocyclic ring may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), e.g., a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28. "heterocycloalkyl" also includes heterocycles that are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo moieties are pyrimidinonyl and 1,1-dioxo-thiomorpholinyl.

The heterocycle groups herein are optionally substituted independently with one or more substituents described herein.

The term "heteroaryl" is meant on or more aromatic ring systems of 5-, 6-, or 7-membered rings containing one or more heteroatoms independently selected from nitrogen, oxygen, and sulfur. Examples of heteroaryl groups are pyridinyl (including, e.g., 2-hydroxypyridinyl), imidazolyl, imidazopyridinyl, pyrimidinyl (including, e.g., 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or .beta.-carboline.

The term "halo" or "halogen" is defined as fluoro, bromo, chloro, and iodo.

The term "optionally selected" means that any one or more hydrogen atoms on the designated atom or group may or may not be replaced by a moiety other than hydrogen.

The term "pharmaceutically acceptable salt", as used herein, refers to pharmaceutically acceptable organic or inorganic salts or zwitterionic forms of a compound of the invention. The phrase "pharmaceutically acceptable" indicates that the substance or composition must be compatible chemically and/or toxicologically, with the other ingredients comprising a formulation, and/or the mammal being treated therewith. The salts can be prepared in situ during the final isolation and purification of the compound of the invention or by separately reacting the purified compound in its free base form with a suitable organic or inorganic acid. Various pharmaceutically acceptable salts are well known in the art (see: Berge S M et al., "Pharmaceutical Salts." *J. Pharm. Sci.* 1977, 66, 1-19, and Haynes D A et al., "Occurrence of pharmaceutically acceptable anions and cations in the Cambridge Structural Database," *J. Pharm. Sci* 2005, 94, 2111-2120, which are hereby incorporated herein by reference). For example, the list of FDA-approved commercially marketed salts includes acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide. Pharmaceutically acceptable salts of compounds of the invention generally are preferred in the methods of the present invention.

The term "prodrug" as used herein refers to compounds that are rapidly transformed in vivo to yield a compound having structural formula (I) and (II), for example, by hydrolysis in blood. A thorough discussion is provided in Higuchi et al., Pro-drugs as Novel Delivery Systems, Vol. 14 of the A.C.S. Symposium Series, and in Roche (ed.), "Bioreversible Carriers in Drug Design", American Pharmaceutical Association and Pergamon Press, (1987), both of which are hereby incorporated by reference. Prodrugs can be converted into a pharmacologically active form through hydrolysis of, for example, an ester or amide linkage, thereby introducing or exposing a functional group on the resultant product. Prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, acetate, chemotherapeutic hormonal or antibody agents. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

Another aspect of the invention is to provide a method for selectively or specifically inhibiting human class I PI3Ks' activity therapeutically or prophylactically, and thereby promote medical treatment of diseases mediated by human PI3Kδ and/or PI3Kγ dysfunction, comprising administering to a mammal in need of such treatment an effective amount of a compound of formula (I) and (II). In some embodiments, the disease or condition may be associated or mediated by PI3Kδ and/or PI3Kγ activities. In certain embodiments, the disease or condition is associated or mediated by PI3Ks. In some embodiments, the disease or condition is an inflammatory disorder, an autoimmune disease, or a cancer. In certain other embodiments, the disease or condition is type II diabetes. In other embodiments, the disease or condition is an autoimmune disease. In additional embodiments, the disease or condition is a cancer, a relapsed cancer after treatment with chemotherapy, and a solid tumor. In additional embodiments, the disease or condition is related to excessive or destructive immune-reactions, such as asthma, rheumatoid arthritis, multiple sclerosis, lupus, psoriasis, or chronic obstructive pulmonary disease (COPD). In other embodiments, the disease or condition is related to bone disorder, inflammatory disease, immune disease, nervous system disease (e.g., a neuropsychiatric disorder), metabolic disease, respiratory disease, thrombosis, and cardiac disease.

Another aspect of the present invention provides methods of preventing or treating a hyperproliferative disorder, comprising administering to a mammal in need of such treatment an effective amount of a compound of formula (I) and (II), alone or in combination with one or more additional compounds having anti-hyperproliferative properties. Examples of such hyperproliferative disease or disorder include, but are not limited to, cancer and/or relapsed cancer after treatment with chemotherapy. In certain embodiment, the cancer or relapsed cancer after treatment with chemotherapy is lymphoma, leukemia, or solid tumor. The solid tumor is selected from the group consisting of pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors, bone cancer, and soft tissue sarcoma. In some embodiments, The solid tumor is from non-small cell lung cancer, small cell lung cancer, colon cancer, CNS cancer, melanoma, ovarian cancer, renal cancer, prostate cancer, or breast cancer.

The term "treating", as used herein, refers to reversing, alleviating, inhibiting the progress of, or preventing the disorder or condition to which such term applies, or preventing one or more symptoms of such condition or disorder. The term "treatment", as used herein, refers to the act of treating, as "treating" is defined immediately above.

"Inflammatory disorder" as used herein refers to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis. "Inflammation" as used herein refers to a localized, protective response elicited by injury or destruction of tissues, which serves to destroy, dilute, or wall off (sequester) both the injurious agent and the injured tissue. Inflammation is associated with an influx of leukocytes and/or neutrophil chemtaxis. Inflammation can result from infection with pathogenic organisms and viruses, and from noninfectious means such as trauma or reperfusion following myocardial infarction or stroke, immune response to foreign antigen, and autoimmune responses. Accordingly, inflammatory disorders amenable to the invention encompass disorders associated with reactions of the specific defense system (i.e., the component of the immune system that reacts to the presence of specific antigens) as well as with reactions of the nonspecific defense system (e.g., granulocytes, and macrophages). In certain embodiments, the inflammatory disease or the immune disease is selected from asthma, emphysema, allergy, dermatitis, rheumatoid arthritis, psoriasis, lupus erythematosus, graft versus host disease, inflammatory bowel disease, eczema, scleroderma, Crohn's disease, or multiple sclerosis.

"Autoimmune disease" as used herein refers to any group of disorders in which tissue injury is associated with humoral or cell-mediated responses to the body's own constituents. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), Sjoegren's syndrome, or autoimmune hemolytic anemia. "Allergic disease" as used herein refers to any symptoms, tissue damage, or loss of tissue function resulting from allergy.

The terms "cancer" refers to or describes the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Because of their unexpected inhibitory activity selectively against class I PI3Ks, the compounds of the present invention are also useful research tools for studying the mechanism of action of those kinases, both in vitro and in vivo, in immuno-oncology.

The above-identified methods of treatment are preferably carried out by administering a therapeutically effective amount of a compound of formula (I) and (II) to a subject in need of treatment. Compounds of the present invention are potent and selective inhibitors of class I PI3Ks. Many of the compounds of the present invention are selective inhibitors of PI3Kδ, which is to say that they inhibit PI3Kδ more potently than they inhibit other class I PI3Ks such as PI3Kα. However, compounds of the present invention also may inhibit PI3Kγ at similar concentrations to those necessary for inhibition of PI3Kδ. Preferred embodiments of the present invention are compounds of formula (I) and (II) are at least about 100-fold selective for inhibition of p110δ relative to p110α, at least about 40-fold selective relative to p110β. Preferred embodiments of the present invention are compounds of formula (I) and (II) possess an $IC_{50}$ value for the inhibition of PI3Kδ and/or PI3Kγ of less than 10 μM, preferably less than 1 μM, even more preferably less than 0.1 μM, most preferably less than 0.05 μM. The compounds are readily synthesized and can be administered by a variety of routes, including orally, transdermally, or by injection or inhalation. In some embodiments, it is administered orally. The compounds of the invention are members of the class of compounds of formula (I) and (II).

The term "therapeutically effective amount" of a compound of the present invention or a pharmaceutically acceptable salt, isomer, prodrug, isotopiically-labeled derivate, or solvate thereof, means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of PI3Kδ activity. The therapeutically effective amount may vary depending on the subject, and disease or condition being treated, the weight and age of the subject, the severity of the disease or condition, and the manner of administering, which can readily be determined by one or ordinary skill in the art.

This invention provides a pharmaceutical composition comprising a compound of formula (I) and (II) and a pharmaceutically acceptable carrier, diluent, or excipient therefor. As used herein, a pharmaceutically acceptable carrier or diluent refers to a carrier or diluent that does not cause significant irritation to an organism and does not abrogate the biological activity and properties of the administered compound. The pharmaceutical composition may further comprise one or more additional therapeutic agents selected based on emerging rational combination strategies as described below.

Another aspect of the invention includes kits comprising a compound of formula (I) and (II), a container, and optionally a package insert or label indicating a treatment. In one embodiment, the container may be a vial, jar, ampoule, preloaded syringe, or an intravenous bag. The term "package insert" refers to instructions customarily included in commercial packages of therapeutic products, that contain information about the indications, usage, dosage, administration, contraindications and/or warnings concerning the use of such therapeutic products. Suitable containers include, e.g., bottles, vials, syringes, blister pack, etc. The container may be formed from a variety of materials such as glass or plastic Another aspect of the invention includes novel intermediates useful for preparing compounds of formula (I) and (II). Such novel intermediates are exemplified as: compound 5 in Example 1, compound 35 in Example 5, compound 52 in Example 8, and compound 58 in Example 9. The preparation and the formation of 5- to 7-membered ring, as depicted in Schemes 1, 4, 6, and 7, were performed with modifications based on the chemistry introduced for the synthesis of pyrrolidine and piperdine alkaloids and nicotine analogs (*J. Org. Chem.* 2001, 66, 6305-6312; *Chin. J. Chem.* 2012, 30, 2813; incorporated herein by reference).

An illustration of the preparation of compounds of the present invention is shown in Schemes 1-7 below. Specific non-limiting examples of compounds of this invention are provided below. The examples presented below are intended to illustrate particular embodiments of the invention, and are not intended to limit the scope of the specification or the claims in any way.

DETAILED DESCRIPTION OF THE INVENTION

Compound Preparation

The compounds of formula (I) and (II) may be prepared by the synthetic sequence shown in Schemes 1 to 7 below. 6-chloro-7,9-dimethyl-7H-purin-8(9H)-one, used for the synthesis of compound 13 in Table 1 below, was prepared based on the procedures reported (*Synthesis* 2014, 46, 660). A skilled artisan will appreciate that other routes of synthesis may be employed as well. In particular, other routes of synthesis may in fact be applied to certain aspects of the present invention. The skilled artisan is referred to general textbooks, such as March's Advanced Organic Chemistry (Michael B. Smith & Jerry March, Wiley-Interscience, 2000), The Practice of Medicinal Chemistry (Camile G. Wermuth, Academia Press, 2003) and Protective Groups in Organic Synthesis (Theosora W. Greene & Peter G. M. Wuts; John Wiley & Sons Inc, 1999).

Unless otherwise noted, all reagents, starting materials and solvents were obtained from commercial suppliers and used without further purification. Concentration or evaporation refers to evaporation under vacuum using a Buchi rotatory evaporator. Reaction products were purified by silica-gel chromatography with the solvent system indicated, or by HPLC purification using a C18 reverse phase semi-preparative HPLC column with solvent A (0.1% of TFA in water) and solvent B (0.1% of TFA in $CH_3CN$) as eluents. All final products have at least 95% purity as determined by analytical HPLC analysis with UV detection at 210 nm and/or 254 nm. Reported yields are isolated yields.

Analytical HPLC analysis was performed on an Agilent 1100 HPLC with a phenomenex Luna C18 (2) column (3 micron, 150×4.6 mm id) at a flow rate of 0.6 mL/min, eluting with a binary solvent system A and B using a 5%-70% B in 20 min gradient elution (A: Milli-Q water with 0.1% TFA; B: $CH_3CN$ with 0.1% TFA). NMR spectra were recorded on a Bruker AV-300 300 MHz NMR instrument using DMSO-$d_6$ or $CDCl_3$ with TMS as an internal standard. Mass spectra data was obtained with Bruker Esquire Liquid Chromatography-Ion Trap Mass Spectrometer. Chiral HPLC analysis was done with Chiralpak ID-3 or Chiralcel OD-H columns, eluting with isopropanol in hexane.

The following abbreviations are used in the synthetic examples: aq (aqueous), h (hour), min (minutes), sat'd (saturated), THF (tetrahydrofuran), rt (room temperature), $Et_3N$ (triethylamine), n-BuOH (n-butyl alcohol), NaCl (sodium chloride), $MgSO_4$ (magnesium sulfate), $CDCl_3$ (deuterated chloroform), $H_2O$ (water), HCl (hydrochloric acid), MeOH (methanol), NaOH (sodium hydroxide), TFA (trifluoroacetic acid), $Na_2CO_3$ (sodium carbonate), $CH_2Cl_2$ (methylene chloride), EtOAC (ethyl acetate), DMF (dimethylformamide), EtOH (ethanol), DMSO (dimethyl sulfoxide), DMSO-$d_6$ (dimethyl sulfoxide-$d_6$), $NaHCO_3$ (sodium bicarbonate), HPLC (high performance liquid chromatography), ESI-MS or MS (ESI) (electrospray ionization-mass spectrometry), NMR (nuclear magnetic resonance), DIEA (diisopropylethylamine), brine (saturated aqueous NaCl solution), $NH_4Cl$ (ammonium chloride), $BH_3$-$Me_2S$ (borane dimethyl sulfide complex), DIAD (diisopropyl azodicarboxylate), DPPA (diphenyl phosphoryl azide), $Boc_2O$ (di-tert-butyl dicarbonate), $NaN_3$ (sodium azide), $Pd(PPh_3)_4$ [Tetrakis(triphenylphosphine)palladium(0)], and other similar standard abbreviations are used herein.

Example 1: Synthesis of 3-(1-(9H-purin-6-yl)pyrrolidin-2-yl)-7-fluoro-2-(pyridin-3-yl)quinoline (1)

Compound 1 was prepared according to the procedures set forth in steps 1-6 of Scheme 1 below:

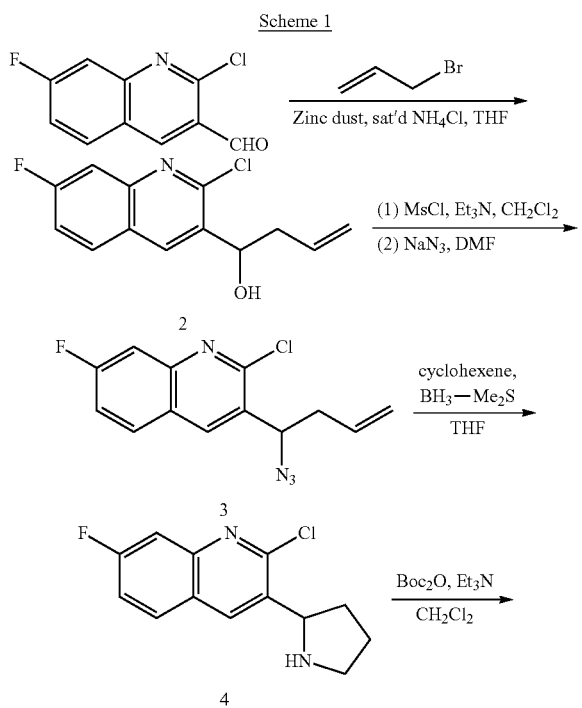

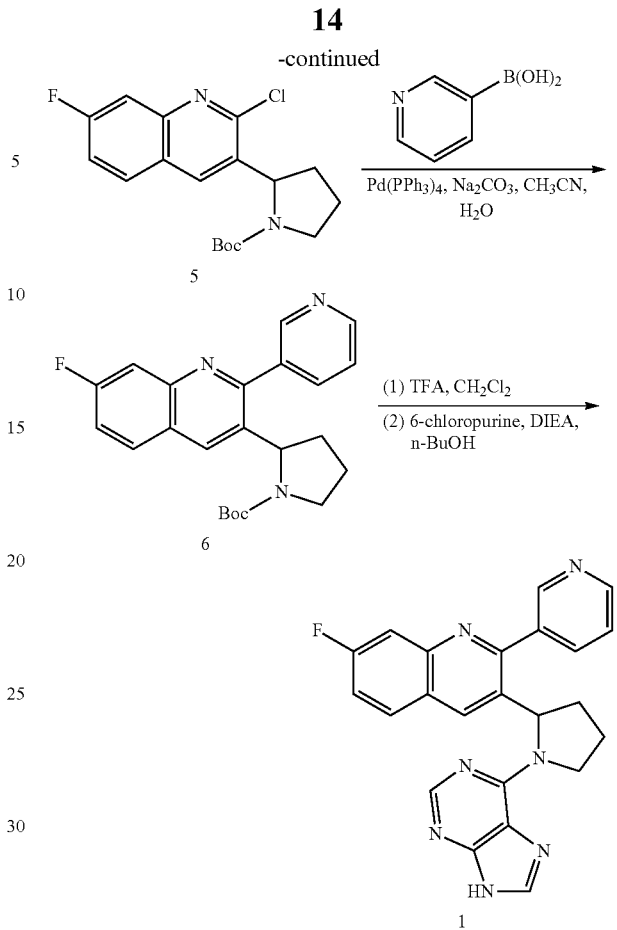

Step 1: 1-(2-chloro-7-fluoroquinolin-3-yl)but-3-en-1-ol (2)

To a solution of 2-chloro-7-fluoroquinoline-3-carbaldehyde (2.0 g, 9.5 mmol; CAS #: 745830-16-4) in THF (191 mL) was added zinc dust (3.1 g, 47.7 mmol) and allyl bromide (1.6 mL, 19.1 mmol), followed by dropwise addition of saturated aqueous ammonium chloride solution (95.4 mL). The reaction mixture was stirred at room temperature for 4 h and filtered via Celite. The filtrate was acidified with 2N HCl (150 mL) and extracted with ethyl acetate (150 mL×1, 100 mL×2). The combined organic extracts was washed with brine (100 mL), dried ($MgSO_4$), and concentrated. Purification by silica-gel column chromatography (25% EtOAc/hexane) yielded the title product (1.7 g, 71%) as a yellow oil. $^1$H NMR (300 MHz, $CDCl_3$) δ 2.41 (m, 2H), 2.84 (m, 1H), 5.27 (m, 3H), 5.86-6.00 (m, 1H), 7.37 (dt, J=8.4 Hz and 2.7 Hz, 1H), 7.66 (dd, J=9.6 Hz and 2.4 Hz, 1H), 7.87 (dd, J=6 Hz and 9 Hz, 1H), 8.39 (s, 1H); MS (ESI): m/z 252.0 (M+H)$^+$.

Step 2: 3-(1-azidobut-3-enyl)-2-chloro-7-fluoroquinoline (3)

To a solution of 1-(2-chloro-7-fluoroquinolin-3-yl)but-3-en-1-ol (1.7 g, 6.75 mmol) in $CH_2Cl_2$ (93 mL) at 0° C. was added $Et_3N$ (1.86 mL, 12.5 mmol), followed by slow addition of methanesulfonyl chloride (0.77 mL, 9.97 mmol). The reaction mixture was stirred at 0° C. under argon for one hour and diluted with water (50 mL). The organic layer was further washed with brine (50 mL×2), dried (MgSO$_4$). Evaporation under reduced pressure afforded the crude mesylate (2.45 g) as a yellow oil, which was immediately used in the next step without purification.

To a solution of this mesylate in DMF (46 mL) was added NaN$_3$ (0.66 g, 10.2 mmol). The resulting mixture was stirred at 60° C. for 3.5 h, diluted with water (120 mL), and extracted with EtOAc (100 mL×2). The combined organic extracts were washed with brine (50 mL), dried (MgSO$_4$) and evaporated to dryness. Purification by silica-gel chromatography with 5% EtOAc/hexane gave the azide 3 (1.4 g, 76%) as a colorless oil. $^1$H-NMR (300 MHz, CDCl$_3$) δ 2.61 (m, 2H), 2.77 (m, 1H), 5.19 (m, 3H), 5.93-5.84 (m, 1H), 7.28 (t, J=4.8 Hz, 1H), 7.41 (dt, J=6 Hz and 2.4 Hz, 1H), 7.68 (dd, J=9.6 Hz and 2.4 Hz, 1H), 7.89 (dd, J=9 Hz and 6 Hz, 1H), 8.23 (s, 1H); MS (ESI): m/z 277.0 (M+H)$^+$.

Step 3: 2-chloro-7-fluoro-3-(pyrrolidin-2-yl)quinoline (4)

To a stirred solution of cyclohexene (1.58 mL, 16.3 mmol) in THF (2.3 mL) at 0° C. was added dropwise 2.0 M BH$_3$-Me$_2$S complex in THF (4.1 mL, 8.2 mmol). The resulting white suspension was stirred for 1 h at 0° C. and then cooled to –15° C. prior to the dropwise addition of 3-(1-azidobut-3-enyl)-2-chloro-7-fluoroquinoline (0.75 g, 2.7 mmol) in THF (7.4 mL). The resulting reaction mixture was allowed to slowly warm to rt. After overnight at rt under argon, the reaction was quenched at 0° C. with MeOH (5 mL) and evaporated to dryness. Purification by silica-gel chromatography with CH$_2$Cl$_2$/MeOH/NH$_4$OH (180:9:1) gave 2-chloro-7-fluoro-3-(pyrrolidin-2-yl)quinoline (0.51 g, 75%) as a pale-yellow solid. $^1$H-NMR (300 MHz, CDCl$_3$) δ 1.91 (m, 2H), 2.51 (m, 1H), 3.22 (m, 2H), 4.65 (t, J=7.5 Hz, 1H), 7.34 (dt, J=8.4 Hz and 2.7 Hz, 1H), 7.65 (dd, J=9.6 Hz and 2.4 Hz, 1H), 7.84 (dd, J=9.3 Hz and 6.3 Hz, 1H), 8.47 (s, 1H).

Step 4: tert-butyl 2-(2-chloro-7-fluoroquinolin-3-yl)pyrrolidine-1-carboxylate (5)

To a solution of 2-chloro-7-fluoro-3-(pyrrolidin-2-yl)quinoline (0.51 g, 2.0 mmol) in CH$_2$Cl$_2$ (25 mL) was added Boc$_2$O (0.66 g, 3.0 mmol), followed by addition of Et$_3$N (0.41 mL, 2.9 mmol). The reaction mixture was stirred at room temperature under argon overnight, and evaporated to dryness. Purification by silica gel chromatography (2% and 4% EtOAc/CH$_2$Cl$_2$) yielded tert-butyl 2-(2-chloro-7-fluoroquinolin-3-yl)pyrrolidine-1-carboxylate (0.44 g, 63%) as a white solid. $^1$H NMR (300 MHz, DMSO-D$_6$) δ 1.04, 1.41 (s, 9H), 1.85, 2.42 (br m, 4H), 3.51 (br m, 1H), 3.73 (br m, 1H), 5.14 (m, 1H), 7.60 (dt, J=9 Hz and 2.7 Hz, 1H), 7.76 (dd, J=10.2 Hz and 2.4 Hz, 1H), 8.22, 8.32 (br s, 2H); MS (ESI): m/z 351.2 (M+H)$^+$.

Step 5: tert-butyl 2-(7-fluoro-2-(pyridin-3-yl)quinolin-3-yl)pyrrolidine-1-carboxylate (6)

A mixture of tert-butyl 2-(2-chloro-7-fluoroquinolin-3-yl)pyrrolidine-1-carboxylate (64 mg, 0.18 mmol), pyridin-3-ylboronic acid (35 mg, 0.28 mmol), Pd(PPh$_3$)$_4$ (21 mg, 0.018 mmol), Na$_2$CO$_3$ (39 mg, 0.36 mmol) in CH$_3$CN (1.35 mL) and water (0.45 mL) was purged with argon for a few minutes and then stirred at 90° C. over 20 hours in a sealed tube. The reaction mixture was cooled to room temperature, and taken up into EtOAc (20 mL) and saturated NaHCO$_3$ (5 mL). The organic layer was washed with brine (50 mL), dried (MgSO$_4$) and evaporated to dryness. Purification by chromatography on silica gel (50% to 90% EtOAc/hexane, and EtOAc) afforded tert-butyl 2-(2-chloro-7-fluoroquinolin-3-yl)pyrrolidine-1-carboxylate (53 mg, 75%) as a pale-yellow oily residue. MS (ESI): m/z 394.2 (M+H)$^+$.

Step 6: 3-(1-(9H-purin-6-yl)pyrrolidin-2-yl)-7-fluoro-2-(pyridin-3-yl)quinoline (1)

To a solution of tert-butyl 2-(2-chloro-7-fluoroquinolin-3-yl)pyrrolidine-1-carboxylate (53 mg, 0.13 mmol) in CH$_2$Cl$_2$ (2 mL) was added TFA (2 mL). The reaction mixture was stirred at room temperature under argon for 1 h. Evaporation and co-evaporation with CHCl$_3$ twice to dryness gave 7-fluoro-2-(pyridin-3-yl)-3-(pyrrolidin-2-yl)quinoline as a pale-yellow oily residue, which was used in the next step without further purification.

A mixture of 7-fluoro-2-(pyridin-3-yl)-3-(pyrrolidin-2-yl)quinoline (TFA salt; 0.13 mmol), DIEA (0.072 mL, 0.4 mmol), and 6-chloropurine (23 mg, 0.15 mmol) in n-BuOH (0.75 mL) was stirred under argon at 115° C. for 22 hours. The reaction mixture was cooled to room temperature and evaporated to dryness. The resulting residues were dissolved in CH$_2$Cl$_2$ (20 mL), washed with H$_2$O (5 mL) and dried (Na$_2$SO$_4$). Purification by silica gel chromatography using CH$_2$Cl$_2$/CH$_3$OH/NH$_4$OH (180:9:1) yielded 3-(1-(9H-purin-6-yl)pyrrolidin-2-yl)-7-fluoro-2-(pyridin-3-yl)quinoline (29 mg, 53% in 2 steps) as a pale yellow solid. $^1$H NMR (300 MHz, DMSO-d$_6$) δ 1.83, 1.91, 2.16 (br m, 4H), 1.95 (bm, 4H), 3.79, 4.22, 4.61 (br m, 2H), 5.48, 6.25 (br s, 1H), 7.50 (dt, J=9 Hz and 2 Hz, 1H), 7.61 (dd, J=7.5 Hz and 4.8 Hz, 1H), 7.76 (dd, J=10.2 Hz and 2.4 Hz, 1H), 8.05 (m, 3H), 8.30, 8.45 (br m, 2H), 8.72 (dd, J=4.5 Hz and 1.5 Hz, 1H), 8.99, 9.15 (br m, 1H); MS (ESI): m/z 412.2 (M+H)$^+$; analytical HPLC: 12.0 min (97% pure); chiral analysis (Chiralcel OD-H, 10% i-PrOH/hexane): 1:1 (R/S).

Example 2: Synthesis of 4-amino-6-(2-(7-fluoro-2-morpholinoquinolin-3-yl)pyrrolidin-1-yl)pyrimidine-5-carbonitrile (7)

Compound 7 was prepared according to the procedures set forth in steps 1-3 of Scheme 2 below:

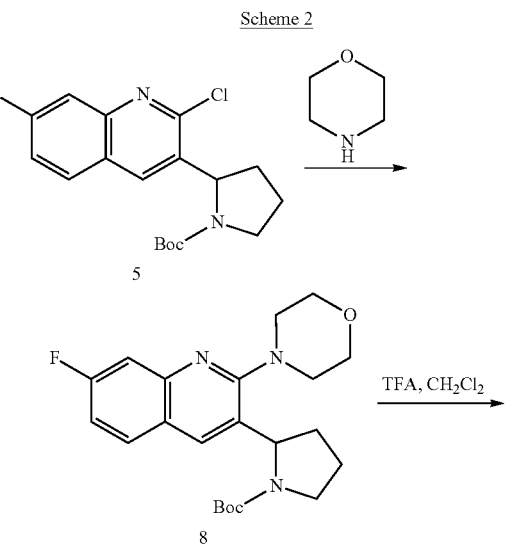

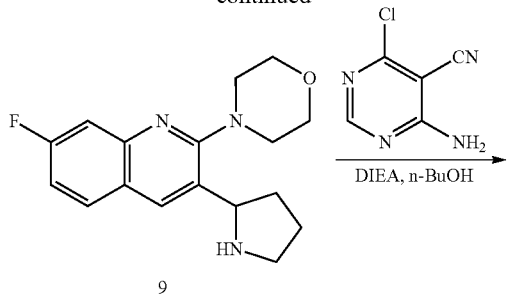

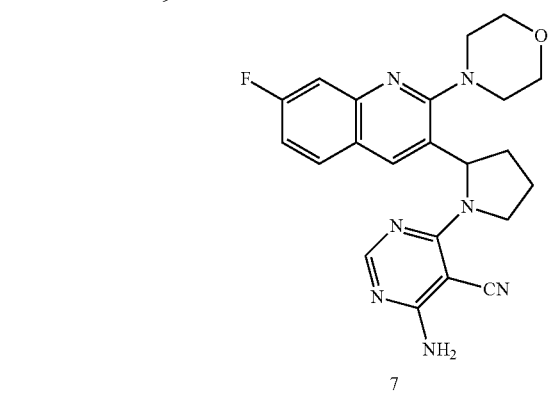

Step 1: tert-butyl 2-(7-fluoro-2-morpholinoquinolin-3-yl)pyrrolidine-1-carboxylate (8)

Intermediate 5 (70 mg, 0.20 mmol) was treated with morpholine (1.0 mL) at 100° C. overnight in a sealed tube. The reaction mixture was cooled to room temperature and evaporated to dryness. Purification by silica-gel chromatography (25% EtOAc/hexane) afforded Compound 8 (75 mg, 93%) as a white solid. MS (ESI): m/z 402.2 (M+H)⁺.

Step 2: 4-(7-fluoro-3-(pyrrolidin-2-yl)quinolin-2-yl)morpholine (9)

To a solution of tert-butyl 2-(7-fluoro-2-morpholinoquinolin-3-yl)pyrrolidine-1-carboxylate (75 mg, 0.19 mmol) in $CH_2Cl_2$ (2 mL) was added TFA (2 mL). The reaction mixture was stirred at room temperature under argon for 1 h. Evaporation and co-evaporation with $CHCl_3$ twice to dryness gave 4-(7-fluoro-3-(pyrrolidin-2-yl)quinolin-2-yl)morpholine (TFA salt; 0.15 g) as a yellow oily residue, which was used in the next step without further purification. MS (ESI): m/z 302.1 (M+H)⁺; analytical HPLC: 14.5 min (100% pure).

Step 3: 4-amino-6-(2-(7-fluoro-2-morpholinoquinolin-3-yl)pyrrolidin-1-yl)pyrimidine-5-carbonitrile (7)

A mixture of 4-(7-fluoro-3-(pyrrolidin-2-yl)quinolin-2-yl)morpholine (TFA salt; 37.7 mg, 0.047 mmol), DIEA (0.072 mL, 0.14 mmol), and 4-amino-6-chloropyrimidine-5-carbonitrile (10.9 mg, 0.071 mmol; CAS #: 60025-09-4) in n-BuOH (0.28 mL) was stirred at 115° C. over 22 hours in a sealed tube. The reaction mixture was cooled to room temperature and evaporated to dryness. HPLC purification using a C18 reverse phase semi-preparative HPLC column ($H_2O$+0.1% TFA/$CH_3CN$+0.1% TFA, 95:5 to 50:50 in 40 min) gave 4-amino-6-(2-(7-fluoro-2-morpholinoquinolin-3-yl)pyrrolidin-1-yl)pyrimidine-5-carbonitrile (TFA salt, 26.5 mg) as a white solid after lyophilization. Further desalting through a Varian StratoSpheres™ PL-HCO3 MP cartridge afforded the title compound 7 (16.6 mg, 84%) as a white powder. MS (ESI): m/z 420.1 (M+H)⁺; analytical HPLC: 16.0 min (>98% pure).

Example 3: Synthesis of 3-(1-(9H-purin-6-yl)pyrrolidin-2-yl)-7-fluoro-2-(pyridin-2-yl)quinoline (10)

Compound 10 was prepared according to the procedures set forth in steps 1-3 of Scheme 3 below:

Scheme 3

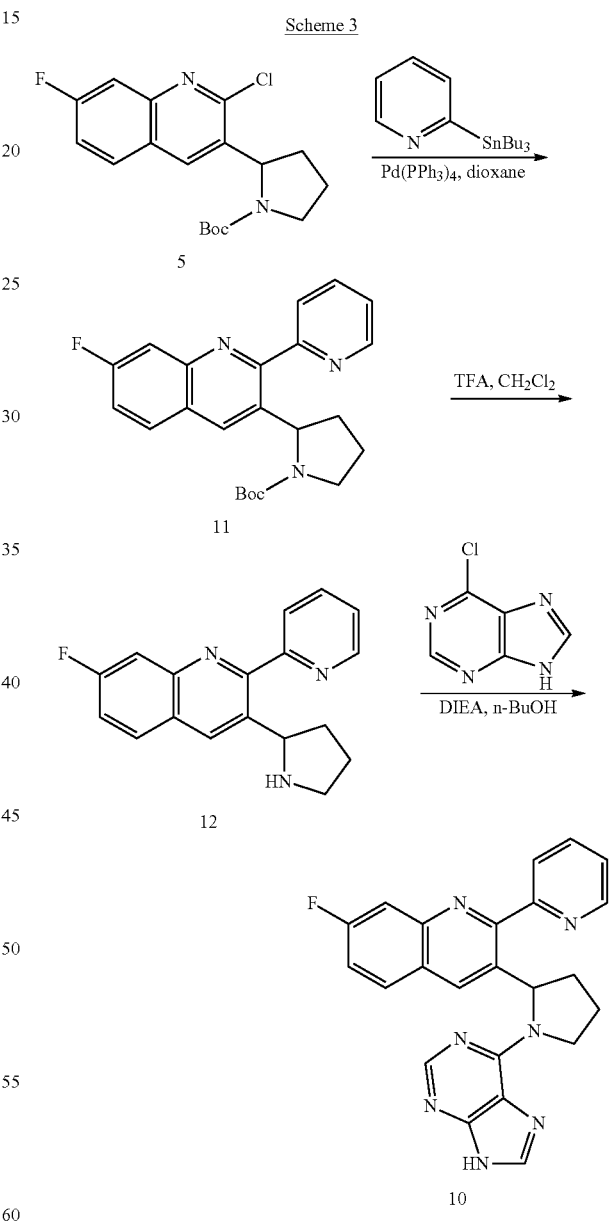

Step 1: tert-butyl 2-(7-fluoro-2-(pyridin-2-yl)quinolin-3-yl)pyrrolidine-1-carboxylate (11)

A mixture of compound 5 (120 mg, 0.35 mmol), 2-(tributylstannyl)pyridine (157 mg, 0.426 mmol), and Pd(PPh₃)₄

(40 mg, 0.035 mmol) in dioxane (3 mL) was purged with argon for 1 min and then stirred at 120° C. over 21 hours in a sealed tube. The reaction mixture was cooled to room temperature, and evaporated to dryness. Purification by silica gel chromatography using EtOAc/CH$_2$Cl$_2$ (5% to 20%) afforded the title compound (41 mg, 30%) as a colorless oily residue. $^1$H NMR (300 MHz, DMSO-d$_6$) δ 0.91, 1.37 (s, 9H), 1.7-2.0 (br m, 4H), 3.71, 3.50 (br m, 2H), 5.24, 5.58 (br m, 1H), 7.56 (m, 2H), 7.80 (dd, J=10.5 Hz and 2.4 Hz, 1H), 8.0 (m, 2H), 8.19, 8.35 (s and t, 2H), 8.72 (d, J=4.5 Hz, 1H); MS (ESI): m/z 394.2 (M+H)$^+$.

Step 2: 7-fluoro-2-(pyridin-2-yl)-3-(pyrrolidin-2-yl)quinoline (12)

To a solution of tert-butyl 2-(7-fluoro-2-(pyridin-2-yl)quinolin-3-yl)pyrrolidine-1-carboxylate (58.7 mg, 0.149 mmol) in CH$_2$Cl$_2$ (1 mL) was added TFA (1 mL). The reaction mixture was stirred at room temperature under argon for 1 h. Evaporation and co-evaporation with CHCl$_3$ twice to dryness gave compound 12 as TFA salts, which was used in the next step without further purification. $^1$H NMR (300 MHz, DMSO-d$_6$) δ 2.09 (m, 1H), 2.21 (m, 1H), 2.35 (m, 1H), 3.50, 3.68 (br s, 2H), 5.06 (m, 1H), 7.64-7.74 (m, 2H), 7.90 (dd, J=10, 5 Hz and 2.7 Hz, 1H), 8.13 (dt, J=7.8 Hz and 1.8 Hz, 2H), 8.25 (m, 2H), 8.80 (m, 1H), 8.88 (s, 1H), 9.3 (br s, 2H).

Step 3: 3-(1-(9H-purin-6-yl)pyrrolidin-2-yl)-7-fluoro-2-(pyridin-2-yl)quinoline (10)

A mixture of compound 12 (TFA salt; 0.149 mmol), DIEA (0.080 mL, 0.447 mmol), and 6-chloropurine (34.6 mg, 0.224 mmol) in n-BuOH (0.9 mL) was stirred under argon at 115° C. over 16 hours. The reaction mixture was cooled to room temperature and evaporated to dryness. The resulting residues were dissolved in CH$_2$Cl$_2$ (10 mL), washed with H$_2$O (5 mL) and dried (Na$_2$SO$_4$). Purification by silica gel chromatography using CH$_2$Cl$_2$/CH$_3$OH/NH$_4$OH (180:9:1) yielded the title compound (32.6 mg, 53%) as an off-white solid. $^1$H NMR (300 MHz, DMSO-d$_6$) δ 1.86, 2.0, 2.35 (br m, 4H), 1.95 (bm, 4H), 3.85, 4.26, 4.58 (br m, 2H), 6.25, 6.32 (br m, 1H), 7.49 (m, 2H), 7.77, 7.9 (br m, 2H), 8.05, 8.14 (m, 1H), 8.05 (m, 5H), 8.74 (br s, 1H); MS (ESI): m/z 412.2 (M+H)$^+$; chiral analysis (Chiralcel OD-H, 10% i-PrOH/hexane): 1:1 (R/S).

Example 4: Synthesis of Compounds 13-30

Compounds 13-30 listed in Table 1 were prepared using the procedures described above in Examples 1-3, starting from compound 5:

TABLE 1

| Compound | Structure | Analytical HPLC Tr (min)/ purity | MS (ESI) [m/z (M + H)$^+$] |
|---|---|---|---|
| 13 | 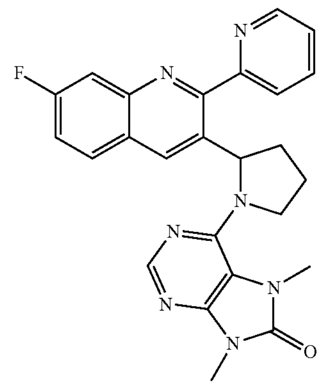 [SMILES: Cn1c(=O)n(C)c2c(N3CCCC3c3cc4ccc(F)cc4nc3-c3ccccn3)ncnc21] | 15.8/95% | 456.2 |
| 14 | 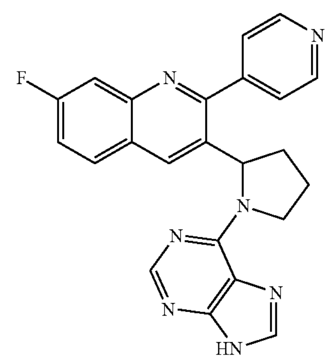 [SMILES: Fc1ccc2cc(C3CCCN3c3ncnc4[nH]cnc34)c(-c3ccncc3)nc2c1] | 13.2/99% | 412.3 |
| 15 | 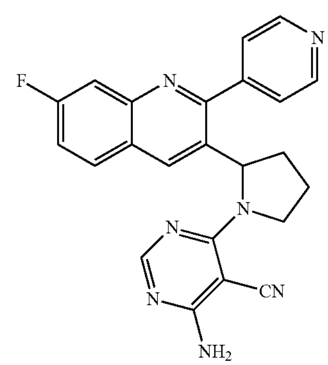 [SMILES: N#Cc1c(N)ncnc1N1CCCC1c1cc2ccc(F)cc2nc1-c1ccncc1] | 14.4/ 100% | 412.1 |
| 16 | 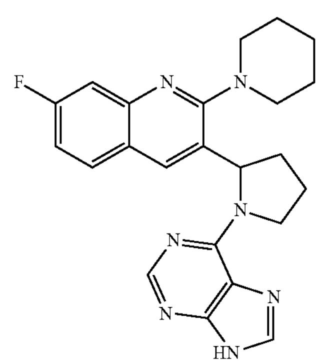 [SMILES: Fc1ccc2cc(C3CCCN3c3ncnc4[nH]cnc34)c(N3CCCCC3)nc2c1] | 14.3/99% | 418.2 |

TABLE 1-continued
| Compound | Structure | Analytical HPLC Tr (min)/purity | MS (ESI) [m/z (M + H)+] |
|---|---|---|---|
| 17 | 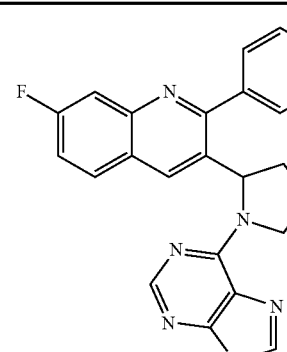 | 14.5/97% | 433.3 |
| 18 | 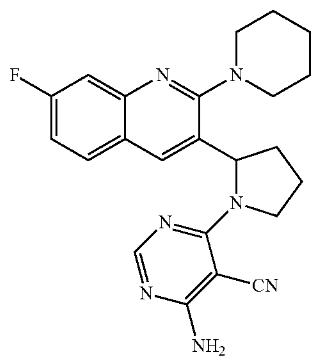 [SMILES: N#Cc1c(N)ncnc1N1CCCC1c1cc2ccc(F)cc2nc1N1CCCCC1] | 15.9/100% | 418.3 |
| 19 | 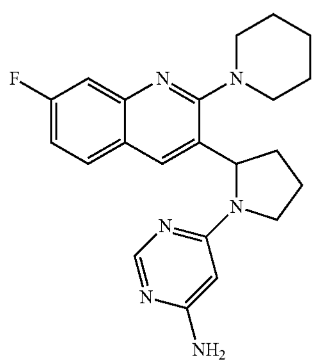 [SMILES: Nc1cc(N2CCCC2c2cc3ccc(F)cc3nc2N2CCCCC2)ncn1] | 14.8/97% | 393.2 |
| 20 | 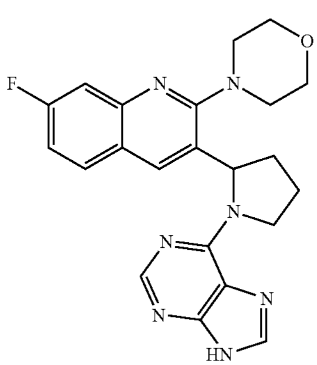 [SMILES: Fc1ccc2cc(C3CCCN3c3ncnc4[nH]cnc34)c(N3CCOCC3)nc2c1] | 14.3/99% | 420.2 |
| 21 | 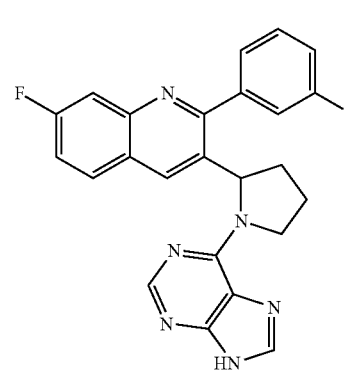 | 15.0/100% | 411.2 |
| 22 | | 17.1/99% | 429.2 |
| 23 | | 16.0/100% | 441.2 |
| 24 | | 14.5/100% | 429.3 |

TABLE 1-continued
| Compound | Structure | Analytical HPLC Tr (min)/purity | MS (ESI) [m/z (M + H)+] |
|---|---|---|---|
| 25 | 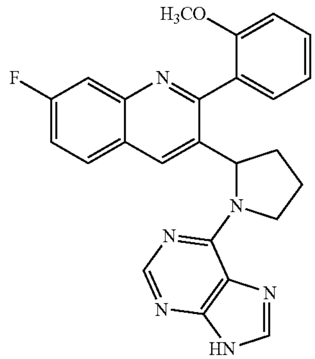 [SMILES: COc1ccccc1-c1nc2cc(F)ccc2cc1C1CCCN1c1ncnc2[nH]cnc12] | 14.7/99% | 441.3 |
| 26 | 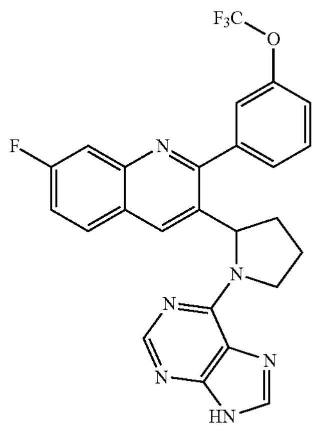 [SMILES: Fc1ccc2cc(C3CCCN3c3ncnc4[nH]cnc34)c(-c3cccc(OC(F)(F)F)c3)nc2c1] | 19.6/98% | 495.3 |
| 27 | 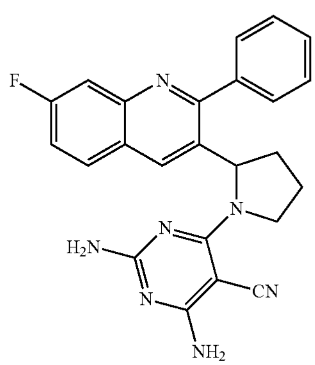 [SMILES: N#Cc1c(N)nc(N)nc1N1CCCC1c1cc2ccc(F)cc2nc1-c1ccccc1] | 16.4/99% | 426.4 |
| 28 | 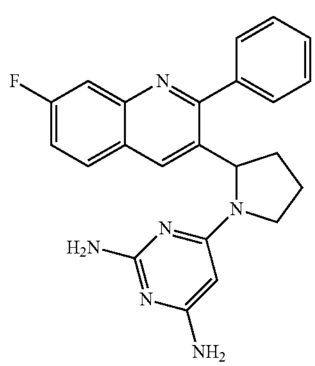 [SMILES: Nc1cc(N2CCCC2c2cc3ccc(F)cc3nc2-c2ccccc2)nc(N)n1] | 16.3/97% | 401.2 |
| 29 | 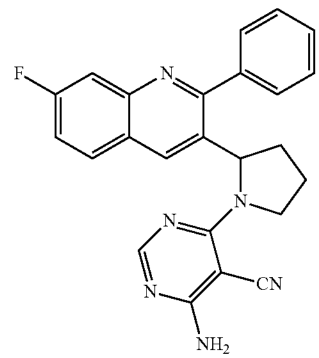 [SMILES: N#Cc1c(N)ncnc1N1CCCC1c1cc2ccc(F)cc2nc1-c1ccccc1] | 16.9/99% | 411.1 |
| 30 | 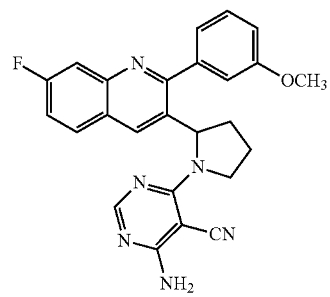 [SMILES: COc1cccc(-c2nc3cc(F)ccc3cc2C2CCCN2c2ncnc(N)c2C#N)c1] | 17.5/98% | 441.1 |
Example 5: Synthesis of 3-(1-(9H-purin-6-yl)-1,2,3,6-tetrahydropyridin-2-yl)-7-fluoro-2-phenylquinoline (31)
Compound 31 was prepared according to the procedures, starting from compound 3, set forth in steps 1-7 of Scheme 4 below:
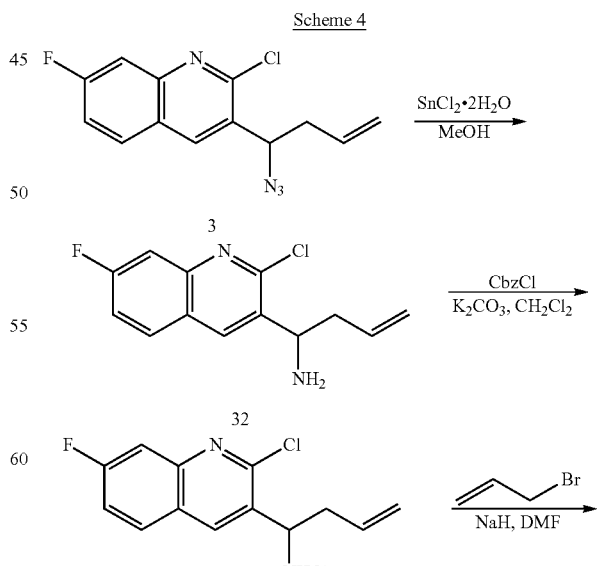
Scheme 4

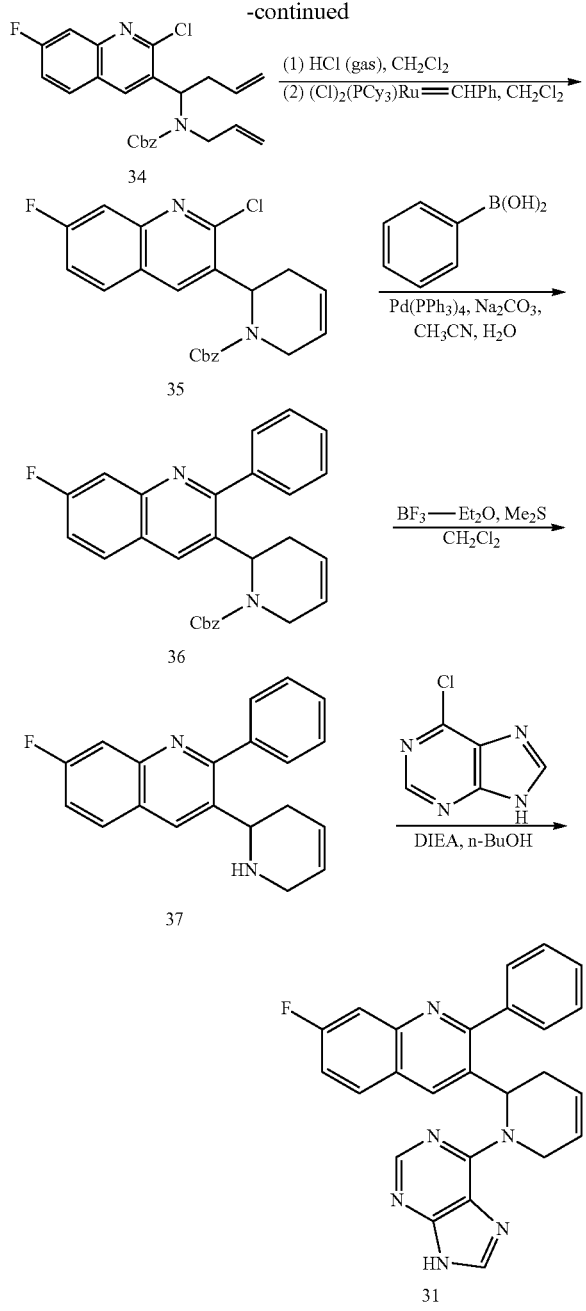

¹H NMR (300 MHz, CDCl₃) δ 2.32 (m, 1H), 2.72 (m, 1H), 4.58 (dd, J=8.4 Hz and 3.9 Hz, 1H), 5.24 (t, J=9.9 Hz, 1H), 5.88 (m, 1H), 7.21 (t, J=14.4 Hz, 1H), 7.37 (dt, J=8.7 Hz and 2.4 Hz, 2H), 7.66 (dd, J=9.9 Hz and 2.4 Hz, 1H), 7.85 (dd, J=9.9 Hz and 2.4 Hz, 1H), 8.41 (s, 1H); MS (ESI): m/z 250.9 (M+H)⁺.

Step 2: benzyl 1-(2-chloro-7-fluoroquinolin-3-yl) but-3-enylcarbamate (33)

To a solution of 1-(2-chloro-7-fluoroquinolin-3-yl)but-3-en-1-amine (1.23 g, 4.91 mmol) in CH₂Cl₂ (32 mL) at 0° C. was added Na₂CO₃ (0.63 g, 5.95 mmol) and benzyl chloroformate (0.85 mL, 5.95 mmol). After stirring for 30 min at room temperature, the reaction mixture was quenched with saturated aqueous NaHCO₃ (50 mL). The aqueous layer was extracted with CH₂Cl₂ (50 mL×3). The combined organic extracts were dried (MgSO₄) and concentrated under reduced pressure. Purification by silica-gel chromatography (25% EtOAc/hexane) gave the title compound 33 (1.4 g, 74%) as an off-white solid. MS (ESI): m/z 385.2 (M+H)⁺.

Step 3: benzyl allyl(1-(2-chloro-7-fluoroquinolin-3-yl)but-3-enyl)carbamate (34)

To a stirred solution of benzyl 1-(2-chloro-7-fluoroquinolin-3-yl)but-3-enylcarbamate (0.78 g, 2.0 mmol) in dry DMF (20 mL) at 0° C. was added NaH (60% dispersion in mineral oil; 0.48 g, 12.1 mmol). After stirring at 0° C. under argon for 10 min, allyl bromide (0.53 mL, 6.1 mmol) was added. The reaction mixture was stirred under argon for 30 min at room temperature, quenched with water (50 mL) and extracted with CH₂Cl₂ (50 mL×3). The combined extracts were washed with brine (25 mL), dried (MgSO₄) and evaporated. Purification by flash chromatography (25% EtOAc/hexane) afforded the title compound (0.85 g, 98%) as an off-white solid. ¹H NMR (300 MHz, CDCl₃) δ 2.89 (br s, 2H), 3.66 (dd, J=15.9 Hz and 6.6 Hz, 1H), 3.91 (dd, J=15.3 Hz and 4.5 Hz, 1H), 4.80 (m, 2H), 5.10 (t, J=10.2 Hz, 1H), 5.22 (m, 2H), 5.60 (t, J=7.8 Hz, 1H), 5.62, 5.79 (br s, 2H), 7.38 (m, 5H), 7.66 (dd, J=9.9 Hz and 2.7 Hz, 2H), 7.80, 8.12, 8.23 (br s, 3H); MS (ESI): m/z 425.1 (M+H)⁺.

Step 4: benzyl 6-(2-chloro-7-fluoroquinolin-3-yl)-5, 6-dihydropyridine-1(2H)-carboxylate (35)

A solution of benzyl allyl(1-(2-chloro-7-fluoroquinolin-3-yl)but-3-enyl)carbamate (0.85 g, 2.0 mmol) in CH₂Cl₂ (18 mL) was treated with HCl gas for 1 min, and then evaporated to dryness. To the resulting residue in CH₂Cl₂ (50 mL) was added bis(tricyclohexylphosphine)benzylidene ruthenium dichloride (0.1 g, 0.125 mmol). The reaction mixture was stirred at 50° C. under argon for 4 h, and then cooled to room temperature before adding saturated aqueous NaHCO₃ (50 mL) and CH₂Cl₂ (50 mL). The organic extract was concentrated in vacuo, and purified by silica-gel chromatography (25% EtOAc/hexane) to give the desired product (0.70 g, 80%) as a yellow oil. ¹H NMR (300 MHz, CDCl₃) δ 2.58 (br m, 2H), 2.88 (br m, 1H), 3.92 (m, 1H), 4.38 (dd, J=18.6 Hz and 3.3 Hz, 1H), 5.17 (s, 2H), 5.90 (m, 2H), 5.60 (br m, 3H), 7.3 (m, 5H), 7.35 (dt, J=8.4 Hz and 2.7 Hz, 1H), 7.65 (dd, J=9.6 Hz and 2.4 Hz, 1H), 7.76 (dd, J=9.0 Hz and 6.0 Hz, 1H), 7.89 (s, 1H); MS (ESI): m/z 397.2 (M+H)⁺.

Step 5: benzyl 6-(7-fluoro-2-phenylquinolin-3-yl)-5, 6-dihydropyridine-1(2H)-carboxylate (36)

A mixture of benzyl 6-(2-chloro-7-fluoroquinolin-3-yl)-5,6-dihydropyridine-1(2H)-carboxylate (0.41 g, 1.0 mmol), Step 1: 1-(2-chloro-7-fluoroquinolin-3-yl)but-3-en-1-amine (32)

To a solution of 3-(1-azidobut-3-enyl)-2-chloro-7-fluoroquinoline (1.42 g, 5.13 mmol) in MeOH (26 mL) at 0° C. was added tin(II) chloride dihydrate (3.7 g, 16.4 mmol) in small portions over 30 min. After stirring at room temperature overnight under argon, the solvent was removed under reduced pressure. The resulting residues were taken into CH₂Cl₂ (30 mL) and water (30 mL), and adjusted pH to 13 with 30% NaOH (aq). The aqueous layer was extracted with CH₂Cl₂ (30 mL×4). The combined extracts were dried (MgSO₄) and concentrated under reduced pressure. Purification by silica gel chromatography (5% CH₂Cl₂/CH₃OH) yielded the title compound (1.23 g, 95%) as a yellow solid.

phenylboronic acid (0.19 g, 1.58 mmol), Pd(PPh$_3$)$_4$ (0.12 mg, 0.10 mmol), Na$_2$CO$_3$ (0.22 g, 2.0 mmol) in CH$_3$CN (7.7 mL) and water (2.6 mL) was purged with argon for 1 min and then stirred at 90° C. over 22 hours in a sealed tube. The reaction mixture was cooled to room temperature, and taken up into EtOAc (40 mL) and saturated NaHCO$_3$ (10 mL). The organic layer was washed with brine (10 mL), dried (MgSO$_4$) and evaporated to dryness. Purification by chromatography on silica gel (25% EtOAc/hexane) afforded the title compound (0.3 g, 68%) as a white foam. $^1$H NMR (300 MHz, DMSO-d$_6$) δ 2.2-2.4 (m, 2H), 4.11 (m, 2H), 3.91 (dd, J=15.3 Hz and 4.5 Hz, 1H), 4.80 (m, 2H), 5.10 (t, J=10.2 Hz, 1H), 5.22 (m, 2H), 5.60 (t, J=7.8 Hz, 1H), 3.9, 5.0 (m, 2H), 5.69 (m, 2H), 5.88 (m, 1H), 7.38 (m, 5H), 7.22, 7.29, 7.44 (br s, 10H), 7.55 (dt, J=8.7 Hz and 2.4 Hz, 1H), 7.72 (dd, J=10.5 Hz and 2.4 Hz, 1H), 8.16 (dd, J=9.0 Hz and 6.3 Hz, 1H), 8.20 (s, 1H); MS (ESI): m/z 439.2 (M+H)$^+$.

Step 6: 7-fluoro-2-phenyl-3-(1,2,3,6-tetrahydropyridin-2-yl)quinoline (37)

A solution of benzyl 6-(7-fluoro-2-phenylquinolin-3-yl)-5,6-dihydropyridine-1(2H)-carboxylate (0.2 g, 0.46 mmol) in dry CH$_2$Cl$_2$ (6.4 mL) was treated with dimethyl sulfide (1.37 mL, 18.7 mmol) and boron trifluoride etherate (0.57 mL, 4.5 mmol). The reaction mixture was stirred at room temperature under argon overnight, poured into 10% aqueous NaOH (20 mL) and extracted with CH$_2$Cl$_2$ (10 mL×3). The combined extracts were washed with brine (10 mL), dried (MgSO$_4$), and concentrated in vacuo. Purification by silica-gel chromatography using CH$_2$Cl$_2$/MeOH/NH$_4$OH (180:9:1) yielded the title compound (0.1 g, 71%) as a pale-yellow oily residue. MS (ESI): m/z 305.1 (M+H)$^+$; analytical HPLC: 15.2 min with 98% purity.

Step 7: 3-(1-(9H-purin-6-yl)-1,2,3,6-tetrahydropyridin-2-yl)-7-fluoro-2-phenylquinoline (31)

Compound 31 was prepared according to the procedure described in Step 3 of Example 2, using compound 37 and 6-chloropurine as the starting materials. MS (ESI): m/z 423.4 (M+H)$^+$; analytical hplc: 15.2 min and 15.3 min (95% pure).

Example 6: Synthesis of 4-(3-(1-(9H-purin-6-yl)piperidin-2-yl)-7-fluoroquinolin-2-yl)morpholine (38)

Compound 38 was prepared according to the procedures, starting from compound 35, set forth in steps 1-3 of Scheme 5 below:

Scheme 5

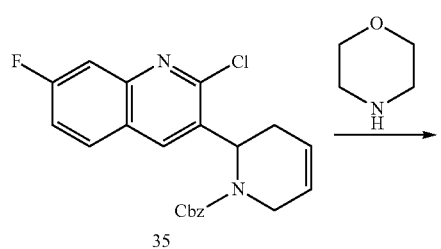

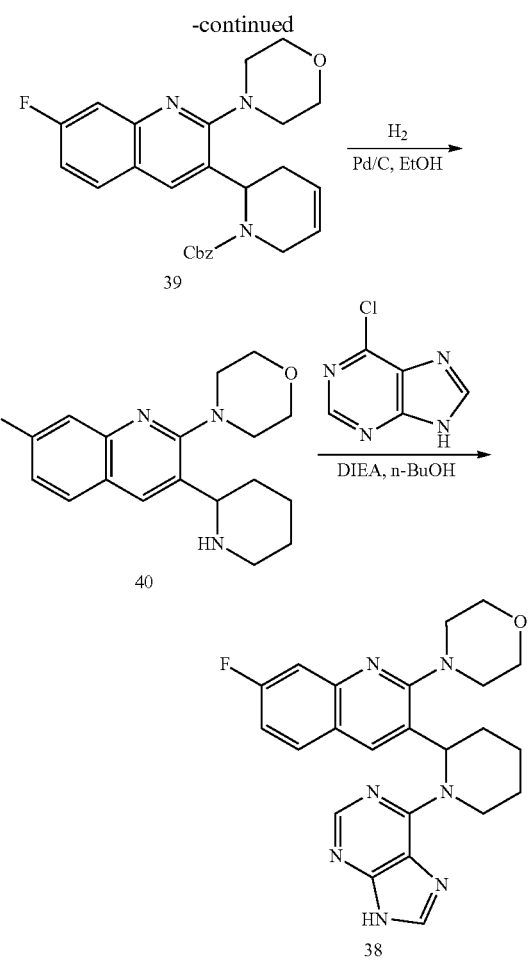

Step 1-2: 4-(7-fluoro-3-(piperidin-2-yl)quinolin-2-yl)morpholine (40)

A solution of compound 39 (66 mg, 0.147 mmol), prepared according to the procedure described in step 1 of Example 2, using compound 35 as the starting material, was dissolved in ethanol (2 mL) and hydrogenated in the presence of 10 wt. % palladium on carbon (15 mg) at room temperature for 20 h. After evaporation, the resulting residues were purified by silica-gel chromatography using CH$_2$Cl$_2$/MeOH/NH$_4$OH (360:9:1, and 180:9:1) to give compound 40 (25 mg, 55%) as a colorless oil. $^1$H NMR (300 MHz, DMSO-d$_6$) δ 1.4-2.4 (m, 6H), 2.63 (m, 2H), 3.13 (m, 4H), 3.4 (m, 2H), 3.80 (m, 5H), 7.31 (dt, J=9.0 Hz and 2.7 Hz, 1H), 7.45 (dd, J=11.1 Hz and 2.7 Hz, 1H), 7.92 (dd, J=9.0 Hz and 6.6 Hz, 1H), 8.34 (s, 1H); MS (ESI): m/z 316.1 (M+H)$^+$; analytical HPLC: 15.5 min (99% pure).

Step 3: 4-(3-(1-(9H-purin-6-yl)piperidin-2-yl)-7-fluoroquinolin-2-yl)morpholine (38)

Compound 38 was prepared according to the procedure described in step 3 of Example 2, using compound 40 as the starting material. MS (ESI): m/z 434.4 (M+H)$^+$; analytical hplc: 16.5 min (96.6% pure).

Example 7: Synthesis of Compound 41-44

Compounds 41-44 listed in Table 2 were prepared using the procedures described above in Examples 5-6:

TABLE 2
| Compound | Structure | Analytical HPLC Tr (min)/purity | MS (ESI) [m/z (M + H)+] |
|---|---|---|---|
| 41 | 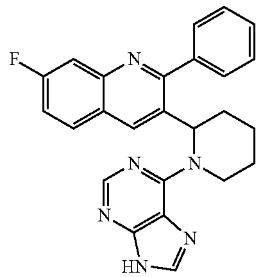 [SMILES: Fc1ccc2cc(C3CCCCN3c3ncnc4[nH]cnc34)c(-c3ccccc3)nc2c1] | 16.4/95% | 425.4 |
| 42 | 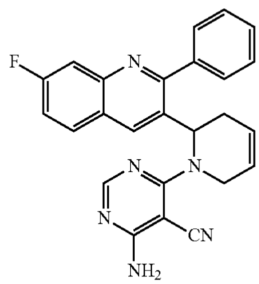 [SMILES: N#Cc1c(N)ncnc1N1CC=CCC1c1cc2ccc(F)cc2nc1-c1ccccc1] | 16.9/100% | 423.0 |
| 43 | 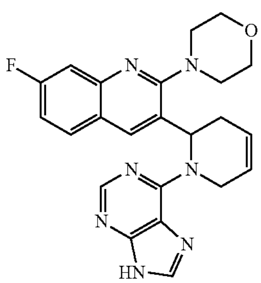 [SMILES: Fc1ccc2cc(C3CC=CCN3c3ncnc4[nH]cnc34)c(N3CCOCC3)nc2c1] | 16.6/97% | 432.3 |
| 44 | 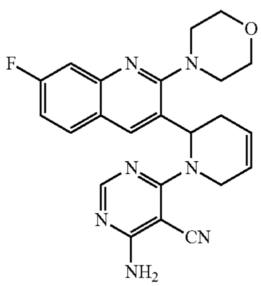 [SMILES: N#Cc1c(N)ncnc1N1CC=CCC1c1cc2ccc(F)cc2nc1N1CCOCC1] | 18.2/99% | 432.3 |
Example 8: Synthesis of 3-(1-(9H-purin-6-yl)azepan-2-yl)-7-fluoro-2-phenylquinoline (45)
Compound 45 was prepared according to the procedures set forth in steps 1-9 of Scheme 6 below:
Scheme 6
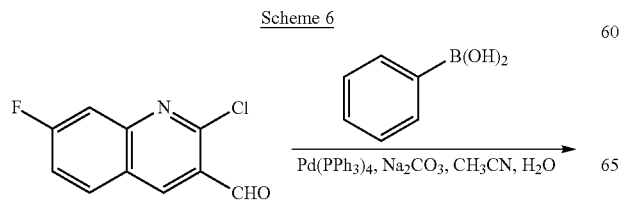
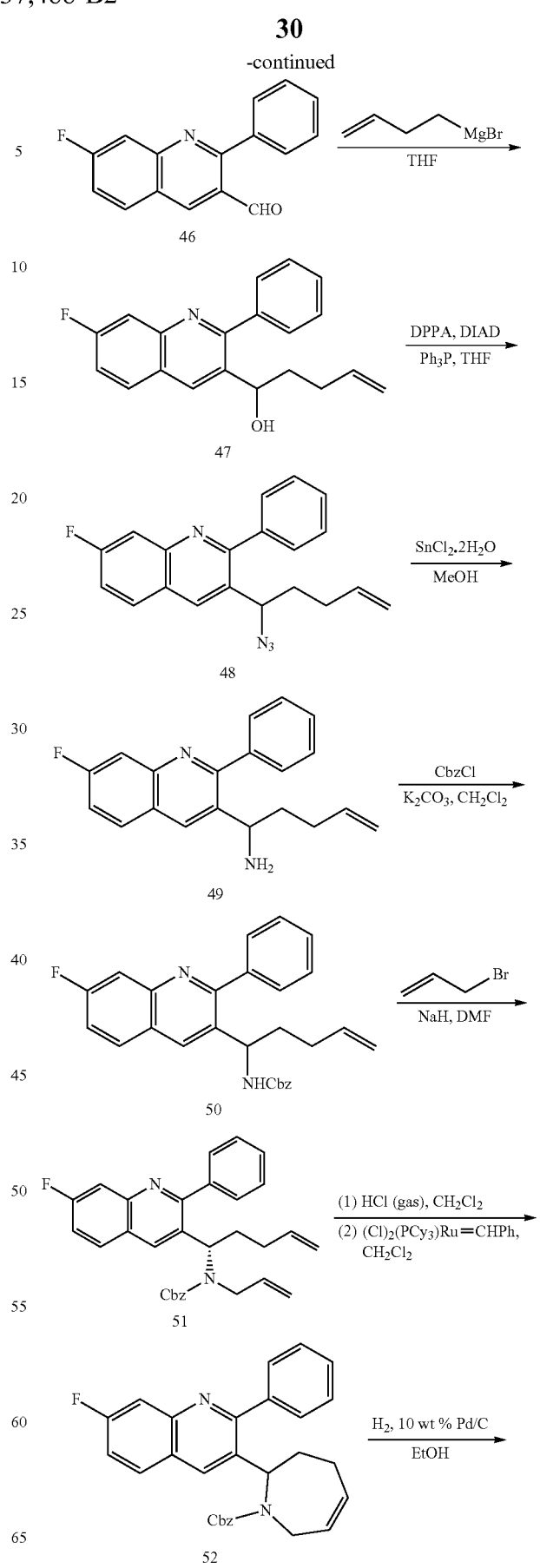

-continued

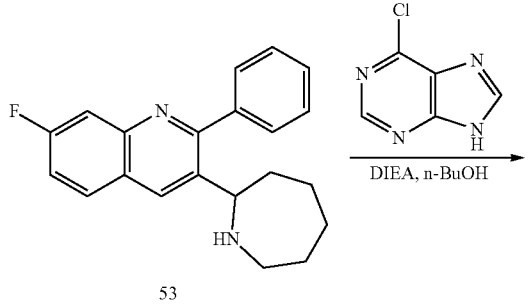

Step 3: 3-(1-azidopent-4-enyl)-7-fluoro-2-phenylquinoline (48)

To a solution of triphenylphosphine (0.487 g, 1.86 mmol) in anhydrous THF (5.6 mL) at 0° C. was added DIAD (0.37 mL, 1.6 mmol). After stirred for 30 min at 0° C., a solution of compound 47 (0.26 g, 0.85 mmol) in THF (5.6 mL) was added, followed by DPPA (0.37 mL, 1.6 mmol). The reaction mixture was stirred at rt overnight and evaporated to dryness. Purification by silica-gel chromatography (5% EtOAc/hexane) gave 48 (0.28 g, 100%) as a colorless oil. MS (ESI): m/z 333.2 (M+H)$^+$, 305.2 (M−N$_2$+H)$^+$.

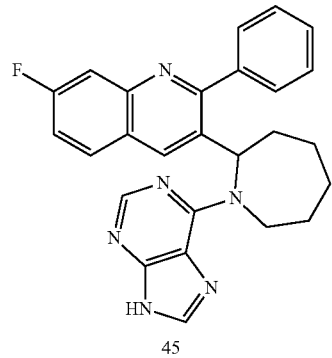

Step 4-9: 3-(1-(9H-purin-6-yl)azepan-2-yl)-7-fluoro-2-phenylquinoline (45)

Compound 45 was prepared using the procedures described above in Example 5, but hydrogenation, as shown in step 2 of Example 6, was used in step 8. MS (ESI): m/z 439.1 (M+H)$^+$, 220, 2 (M$^{2+}$+H); analytical HPLC: 17.9 min (96% pure at 210 nm).

Example 9: Synthesis of (S)-2,4-diamino-6-(2-(8-chloro-2-phenylquinolin-3-yl)pyrrolidin-1-yl)pyrimidine-5-carbonitrile (54)

Compound 54 was prepared according to the procedures set forth in steps 1-8 of Scheme 7 below:

Step 1: 7-fluoro-2-phenylquinoline-3-carbaldehyde (46)

A mixture of 2-chloro-7-fluoroquinoline-3-carbaldehyde (1.0 g, 4.77 mmol; CAS #: 745830-16-4), phenylboronic acid (0.64 g, 5.25 mmol), Pd(PPh$_3$)$_4$ (0.28 g, 0.24 mmol), Na$_2$CO$_3$ (2.53 g, 23.9 mmol) in CH$_3$CN (73 mL) and water (24 mL) was stirred at 100° C. under argon over 23 hours. The reaction mixture was cooled to room temperature, and taken up into EtOAc (150 mL) and water (150 mL). The organic layer was washed with brine (100 mL×2), dried (Na$_2$SO$_4$) and evaporated to dryness. Purification by chromatography on silica gel using EtOAc/hexane (5%, and 10%) afforded the title compound (0.70 g, 58%) as a pale-yellow solid. $^1$H NMR (300 MHz, CDCl$_3$) δ 7.46 (dt, J=8.4 Hz and 2.4 Hz, 1H), 7.6 (m, 3H), 7.70 (m, 2H), 7.86 (dd, J=10.2 Hz and 2.7 Hz, 1H), 8.06 (dd, J=9.0 Hz and 6.0 Hz, 1H), 8.87 (s, 1H), 10.2 (s, 1H).

Step 2: 1-(7-fluoro-2-phenylquinolin-3-yl)pent-4-en-1-ol (47)

To a stirred solution of compound 46 (0.43 g, 1.3 mmol) in THF (7 mL) at −20° C. was added 3-butenylmagnesium bromide (0.5 M in THF; 3.8 mL, 1.9 mmol). After stirred at −20° C. under argon for 22 hours, the reaction mixture was quenched by addition of sat'd NH$_4$Cl (30 mL), slowly warmed to room temperature, and extracted with Et$_2$O (30 mL×2). The organic extracts were washed with water (15 mL), brine (15 mL), dried (Na$_2$SO$_4$), and evaporated to dryness. Purification by silica-gel chromatography with EtOAc/hexane (12.5%, 25%) gave the title compound (0.35 g, 70%) as a white solid. $^1$H NMR (300 MHz, CDCl$_3$) δ 1.8 (m, 2H), 2.1 (m, 1H), 4.8-5.1 (m, 3H), 5.58 (m, 1H), 7.37 (dt, J=8.4 Hz and 2.1 Hz, 1H), 7.51 (m, 5H), 7.66 (dd, J=10.2 Hz and 2.7 Hz, 1H), 7.89 (dd, J=9 Hz and 6 Hz, 1H), 8.46 (s, 1H).

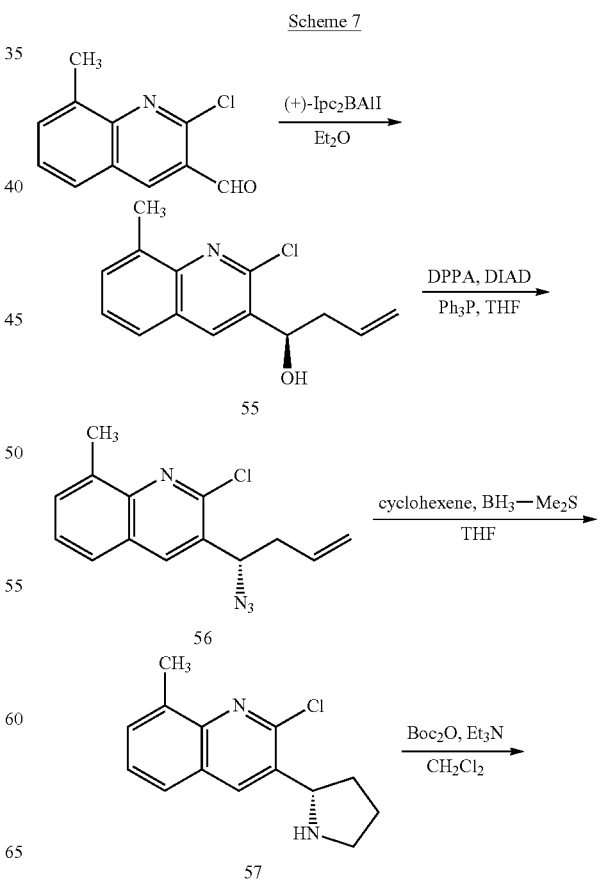

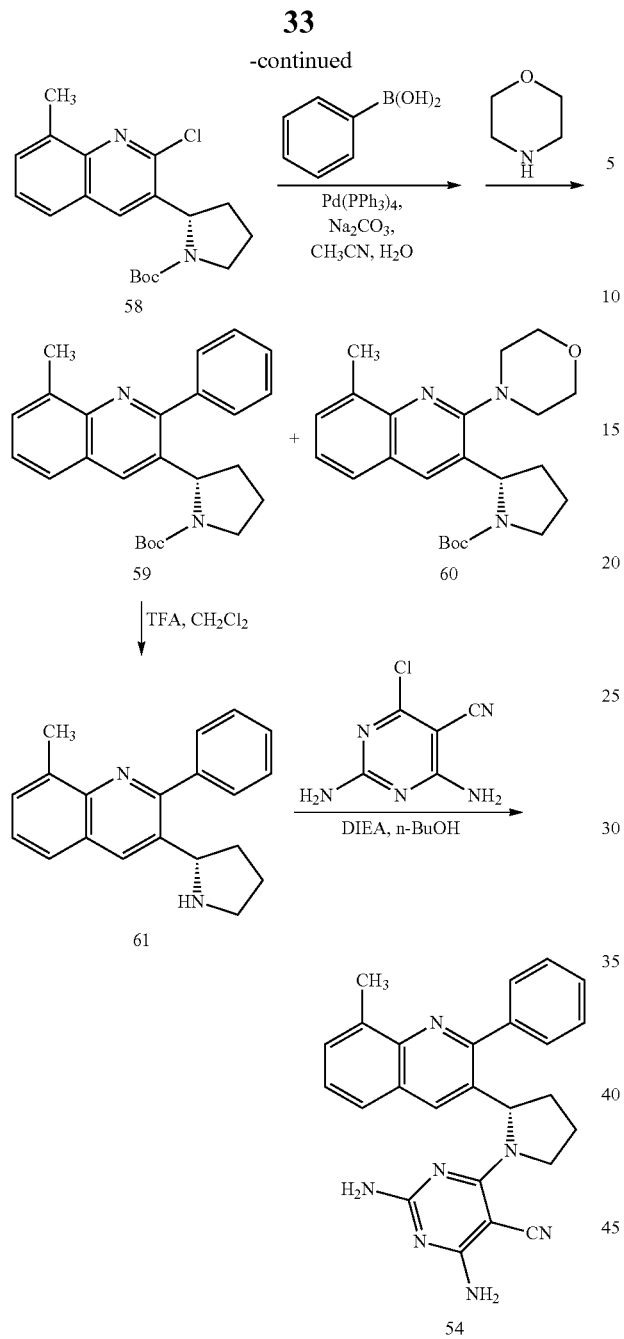

5.2-5.3 (m, 3H), 5.9 (m, 1H), 7.47 (t, J=7.8 Hz, 1H), 7.58 (d, J=6 Hz, 1H), 7.70 (d, J=8.1 Hz, 1H), 8.34 (s, 1H); chiral HPLC (Chiralpak ID-3, 5% i-PrOH/hexane): 1:99 (S/R).

Step 2-4: (S)-tert-butyl 2-(2-chloro-8-methylquinolin-3-yl)pyrrolidine-1-carboxylate (58)

Compound 58 was prepared in 3 steps from the alcohol 55 using the procedure described above in step 3 of Example 8, followed by the procedures described above in steps 3 and 4 of Example 1. MS (ESI): m/z 715.5 (2M+Na)⁺; chiral HPLC (Chiralcel OD-H, 5% i-PrOH/hexane): 93:7 (S/R).

Step 5-6: (S)-tert-butyl 2-(8-methyl-2-phenylquinolin-3-yl)pyrrolidine-1-carboxylate (59), and (S)-tert-butyl 2-(8-methyl-2-morpholinoquinolin-3-yl)pyrrolidine-1-carboxylate (60)

A mixture of (S)-tert-butyl 2-(2-chloro-8-methylquinolin-3-yl)pyrrolidine-1-carboxylate (124 mg, 0.36 mmol), phenylboronic acid (66 mg, 0.54 mmol), Pd(PPh₃)₄ (41 mg), Na₂CO₃ (77 mg) in CH₃CN (2.7 mL) and water (0.9 mL) was stirred at 90° C. under argon over 20 hours. The reaction mixture was cooled to room temperature, and taken up into EtOAc (25 mL) and saturated NaHCO₃ (5 mL). The organic layer was washed with brine (5 mL), dried (MgSO₄) and evaporated to dryness. The resulting residues were treated with morpholine (1.0 mL) at 100° C. overnight. The reaction mixture was cooled to room temperature and evaporated to dryness. Purification by chromatography on silica gel using EtOAc/hexane (15%, and 25%) afforded compound 59 (60 mg, 43%) as a white foam, and compound 60 (62 mg, 44%) as a white solid. Compound 59: MS (ESI): m/z 389.4 (M+H)⁺; compound 60: MS (ESI): m/z 398.7 (M+H)⁺.

Step 7-8: (S)-2,4-diamino-6-(2-(8-methyl-2-phenylquinolin-3-yl)pyrrolidin-1-yl)pyrimidine-5-carbonitrile (54)

Compound 54 was prepared in 2 steps, starting from compound 59, based on the procedures described in Steps 2 and 3 of Example 2, but 4-amino-6-chloropyrimidine-5-carbonitrile was substituted by 2,4-diamino-6-chloropyrimidine-5-carbonitrile prepared as in Example 3 of WO2014/201409 (incorporated herein by reference). MS (ESI): m/z 422.3 (M+H)⁺; analytical hplc: 18.1 min (99% pure); chiral HPLC (Chiralcel OD-H, 5% i-PrOH in hexane): 92:8 (S/R).

Step 1: (R)-1-(2,8-dichloroquinolin-3-yl)but-3-en-1-ol (55)

To a solution of (+)-B-allyldiisopinocampheylborane (1 M in pentane; 10 mL, 10 mmol) in ether (20 mL) at <−90° C. was added 2-chloro-8-methylquinoline-3-carbaldehyde (0.92 g, 4.47 mmol) in small portions to maintain the internal temperature below −90° C. After stirring at <−90° C. for 1 h, the reaction mixture was quenched with methanol (1 mL), and then allowed to warm to room temperature. This mixture was diluted with Et₂O (30 mL), washed with 1 N HCl (30 mL×2) and evaporated to dryness. Purification by silica-gel chromatography using EtOAc/hexane (5% and 10%) gave the alcohol 55 (1.3 g) as a colorless oil; ¹H NMR (300 MHz, CDCl₃) δ 2.4 (m, 2H), 2.8 (S, 3H), 2.83 (m, 1H), Example 10: Synthesis of Compounds 62-69

Compounds 62-69 listed in Table 3 were prepared using the procedures described above in Example 9, starting from 2-chloro-8-methylquinoline-3-carbaldehyde, or 2,8-dichloroquinoline-3-carbaldehyde, or 2-chloro-7-fluoroquinoline-3-carbaldehyde:

TABLE 3

| Compound | Structure | Analytical HPLC Tr (min) | Chiral analysis S/R | MS (ESI) [m/z (M+H)+] |
|---|---|---|---|---|
| 62 | 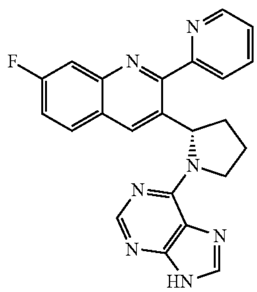 [SMILES: Fc1ccc2cc([C@@H]3CCCN3c3ncnc4[nH]cnc34)c(-c3ccccn3)nc2c1] | 15.0 | 96/4 | 412.2 |
| 63 | 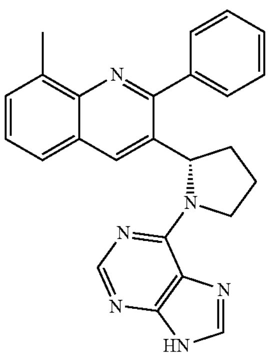 [SMILES: Cc1cccc2cc([C@@H]3CCCN3c3ncnc4[nH]cnc34)c(-c3ccccc3)nc12] | 16.9 | 93/7 | 407.3 |
| 64 | 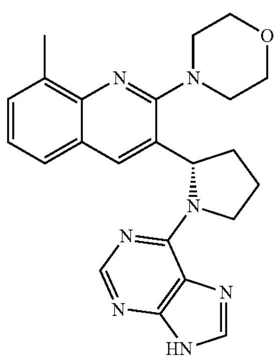 [SMILES: Cc1cccc2cc([C@@H]3CCCN3c3ncnc4[nH]cnc34)c(N3CCOCC3)nc12] | 17.4 | 94/6 | 416.3 |
| 65 | 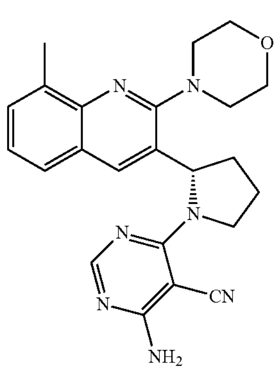 [SMILES: Cc1cccc2cc([C@@H]3CCCN3c3ncnc(N)c3C#N)c(N3CCOCC3)nc12] | 19.3 | 98/2 | 416.3 |
| 66 | 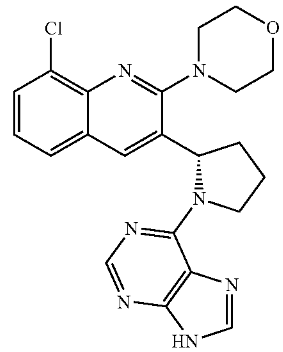 [SMILES: Clc1cccc2cc([C@@H]3CCCN3c3ncnc4[nH]cnc34)c(N3CCOCC3)nc12] | 18.5 | 91/9 | 436.4 |
| 67 | 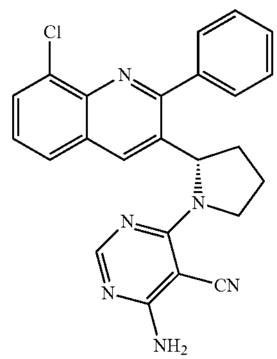 [SMILES: N#Cc1c(N)ncnc1N1CCC[C@H]1c1cc2cccc(Cl)c2nc1-c1ccccc1] | 21.5 | 95/5 | 427.4 |
| 68 | 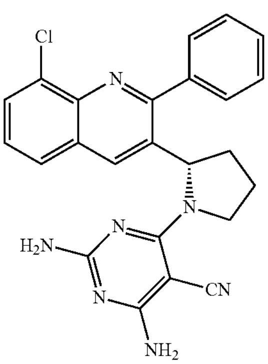 [SMILES: N#Cc1c(N)nc(N)nc1N1CCC[C@H]1c1cc2cccc(Cl)c2nc1-c1ccccc1] | 20.8 | 95/5 | 442.4 |
| 69 | 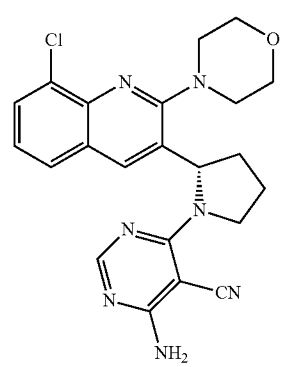 [SMILES: N#Cc1c(N)ncnc1N1CCC[C@H]1c1cc2cccc(Cl)c2nc1N1CCOCC1] | 20.6 | 97/3 | 436.5 |

Biological Characterization of Exemplary Compounds of Formula (I) and (II)

Exemplary compounds of the invention were tested for inhibitory activity and potency against class I PI3Ks (p110α/p85α, p110β/p85α, p110δ/p85α and p110γ) using a cell-free based PI3K HTRF assay. This assay was used to detect the formation of the product 3,4,5-inositol triphosphate molecule (PIP3) by displacement of biotin-PIP3 from an energy transfer complex consisting of Europium labeled anti-GST monoclonal antibody, a GST-tagged pleckstrin homology (PH) domain, biotinylated PIP3 and Streptavidin-Allophycocyanin (APC). Excitation of Europium in the complex results in an energy transfer to the APC and a fluorescent emission at 665 nm. The PIP3 product formed by human PI 3-Kinase activity displaces biotin-PIP3 from the complex resulting in a loss of energy transfer and thus a decrease in signal.

Human class I PI3K isoforms were co-expressed in a Baculovirus infected cell expression system. The PI3K isoforms were assayed in the presence of HEPES (50 mM, pH 7.0), $NaN_3$ (0.02%), BSA (0.01%), orthovanadate (0.1 mM), and DMSO (1%). The exemplary compounds dissolved in DMSO were delivered into the kinase reaction mixture by Acoustic technology (Echo550; nanolitter range), and were pre-incubated for 10 min at room temperature before adding ATP (10 μM) to initiate the reaction. After 30 min at 30° C., the reactions were quenched with a stop solution, incubated overnight with a detection mixture before measuring HTRF (Ex: 320 nm; Em: 615/665 nm). The emission ratio is converted into μM PIP3 production based on PIP3 standard curves, and the nonlinear regression to obtain the standard curve and $IC_{50}$ values are performed using Graphpad Prism software.

The assays were performed at Reaction Biology Corporation, One Great Valley Parkway, Suite 2, Malvern, Pa. 19355, USA.

Example 11: Inhibitory Activity and Potency Against PI3Kδ

Exemplary compounds of the invention were tested their inhibitory activity or potency against PI3Kδ in 10-dose $IC_{50}$ mode with 3-fold serial dilution starting at 1 μM. The control compound, PI-103, was tested in the same conditions. Table 4 below summarizes the $IC_{50}$ values that were collected against PI13Kδ for compounds exemplified in this invention. All $IC_{50}$ values were reported in unites of nM. An $IC_{50}$ value less than 0.0508 nM or 0.508 nM, or higher than 1 mM or 10 mM was estimated based on the best curve fitting available. Empty cells indicate no inhibition or compound activity that could not be fit to an $IC_{50}$ curve.

As demonstrated in Table 4 below, many exemplary compounds of formula (I) and formula (II) are potent inhibitors of PI3Kδ. Preferred compounds of the present invention possess an $IC_{50}$ value for the inhibition of PI3Kδ of less than 10 μM, preferably less than 1 μM, even more preferably less than 0.1 μM, most preferably less than 0.05 μM.

It is worth noting that the unexpected enhancement of the inhibitory activity or potency against PI3Kδ is attributed to the unusual overall shape of the molecules of formula (I) and (II), and the optimal selection of $R_1$, $R_2$, $R_3$, $R_4$, X, and Y defined in formula (I) and (II) in order to bind favorably in the ATP-binding pocket of PI3Kδ. For example, compound 45 exhibits week potency or inhibition against PI3Kδ by simple replacement of the linker between the 3-position of the quinoline and 6-position of purine with a 7-membered ring; compound 13 has week potency or inhibition against PI3Kδ because the 7,9-dimethyl-7H-purin-8(9H)-one moiety is out of the scope of Y defined in formula (I) and (II).

TABLE 4

| Compound | $IC_{50}$ (nM) |
|---|---|
| 1 | 27 |
| 7 | 1.6 |
| 10 | 13 |
| 13 | >1000 |
| 14 | 521 |
| 15 | 62 |
| 16 | 2.2 |
| 17 | 0.9 |
| 18 | 0.1 |
| 19 | |
| 20 | 19 |
| 21 | 0.7 |
| 22 | 0.5 |
| 23 | 11 |
| 24 | 16 |
| 25 | 14 |
| 26 | 207 |
| 27 | <0.05 |
| 28 | >1000 |
| 29 | 1.7 |
| 30 | 4.8 |
| 31 | 103 |
| 38 | 7.1 |
| 41 | 240 |
| 42 | 55 |
| 43 | 6.8 |
| 44 | 6.2 |
| 45 | >1000 |
| 54 | <0.05 |
| 62 | 12.8 |
| 63 | 18 |
| 64 | 1.6 |
| 65 | <0.05 |
| 66 | 1.8 |
| 67 | <0.05 |
| 68 | <0.05 |
| 69 | <0.05 |
| PI-103 | 2.5 |

$IC_{50}$ value for the inhibition of PI3Kδ

Example 12: Selectivity for PI3Kδ Versus Other Class I Isozymes

Exemplary compounds of the invention selected were further tested their inhibitory activity or potency against PI3Kα, PI3Kβ, and PI3Kγ in 10-dose $IC_{50}$ mode with 3-fold serial dilution starting at 10 μM. The control compound, PI-103, was tested with 3-fold serial dilution starting at 10 μM. Table 5 below illustrates the selectivity of the exemplary compounds using the ratios of the $IC_{50}$ values of the compounds against PI3Kα, PI3Kβ, and PI3Kγ related to PI3Kδ. As shown in Table 5, exemplary compounds of formula (I) and (II) selected are selective inhibitors of PI3Kδ and/or PI3Kδ/PI3Kγ. Such unexpected selectivity against PI3Kδ and/or PI3Kγ is attributed to the unusual overall shape of the molecules of formula (I) and (II), and the optimal selection of $R_1$, $R_2$, $R_3$, $R_4$, X, and Y defined in formula (I) and (II) in order to bind favorably in the ATP-binding pocket of PI3Kδ and/or PI3Kγ versus other class I isozymes.

TABLE 5

Selectivity against PI3Kα, PI3Kβ, and PI3Kγ related to PI3Kδ

| Compound | Ratio (α/δ) | Ratio (β/δ) | Ratio (γ/δ) |
|---|---|---|---|
| 1 | | 267 | 39 |
| 7 | 1000 | 344 | 111 |
| 10 | >781 | 519 | 53 |

TABLE 5-continued

Selectivity against PI3Kα, PI3Kβ, and PI3Kγ related to PI3Kδ

| Compound | Ratio (α/δ) | Ratio (β/δ) | Ratio (γ/δ) |
|---|---|---|---|
| 14 | >19 | 4.2 | 3.3 |
| 15 | 138 | 11 | 2.2 |
| 16 | 3360 | 1153 | 145 |
| 17 | 5958 | 1714 | 1.1 |
| 18 | >100000 | 14712 | 955 |
| 20 | 528 | 190 | 18.8 |
| 21 | 12818 | 3550 | 67.5 |
| 22 | 16451 | 8946 | 139 |
| 23 | >926 | 396 | 50 |
| 24 | >613 | 393 | 22 |
| 25 | >694 | 297 | 5.1 |
| 26 | 483 | 39.7 | 12 |
| 27 | >12756 | >2185 | >2.3 |
| 29 | 2170 | 478 | 52.4 |
| 30 | 962 | 631 | 85 |
| 31 |  | >97 | 16 |
| 38 | 529 | 537 | 106 |
| 42 |  | >181 | 103 |
| 43 | 689 | 169 | 39 |
| 44 |  | 297 | 152 |
| 54 | >1801 | >1120 | ~10 |
| 62 | >781 | 520 | 53 |
| 63 | 556 | 264 | 5.6 |
| 64 | 748 | 317 | 48 |
| 65 | >1738 | >789 | >188 |
| 66 | 493 | 250 | 24 |
| 67 | >8583 | 1368 | >5.6 |
| 68 | >545 | >106 | ~10 |
| 69 | >4154 | >111 | >31 |
| PI-103 | 1.5 | 0.86 | 29 |

Therapeutic Uses and Pharmaceutical Compositions of Compounds of the Present Invention The compounds of this invention have useful pharmaceutical and medicinal properties. Many of the compounds of formula (I) and (II) of this invention exhibit significant selective PI3Kδ and/or PI3Kγ inhibitory activity and therefore are of value in the treatment of a wide variety of clinical conditions in which PI3Kδ and/or PI3Kγ are abnormally elevated, or activated or present in normal amounts and activities, but where inhibition of the PI3Ks is desirable to treat a cellular proliferative disorder. Such disorders include, but are not limited to those such as autoimmune, inflammatory and allergic diseases, asthma, COPD, parasitic infections, diabetes, and cancer.

A compound of the present invention may be employed alone or in combination with other therapeutic agents for the treatment of a disease or disorder susceptible to amelioration by inhibition of PI3Ks, such as a hyperproliferative disorder (e.g., cancer). The therapeutic agents used in the combination therapy of the present invention are known to be useful in the treatment of respiratory diseases, allergic diseases, inflammatory or autoimmune diseases, function disorders and neurological disorders and pain, cardiovascular diseases, viral infection, metabolism/endocrine function disorders, bone marrow and organ transplant rejection, myelodysplastic syndrome, myeloproliferative disorders, cancer and hematologic malignancies, leukemia, lymphomas and solid tumors. The solid tumor is selected from the group consisting of pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors, bone cancer, and soft tissue sarcoma. In some embodiments, the solid tumor is selected from non-small cell lung cancer, small-cell lung cancer, colon cancer, CNS cancer, melanoma, ovarian cancer, renal cancer, prostate cancer, and breast cancer.

A compound of the present invention can be administered orally, or by injection or inhalation, and the like. A compound of the present invention can be administered as the neat chemical, but it is typical, and preferable, to administer the compound in the form of a pharmaceutical composition or formulation. Accordingly, the present invention also provides pharmaceutical compositions that comprise a compound of formula (I) and (II) and a biocompatible pharmaceutical carrier, adjuvant, or vehicle. The composition can include a compound of formula (I) and (II) either as the sole active agent or in combination with other therapeutic agents mixed with an excipient or other pharmaceutically acceptable carriers. Carriers and other ingredients can be deemed pharmaceutically acceptable insofar as they are compatible with other ingredients of the formulation and not deleterious to the recipient thereof. Techniques for formulation and administration of pharmaceutical compositions can be found in Remington's Pharmaceutical Sciences, 18th Ed., Mack Publishing Co, Easton, Pa., 1990; and Modern Pharmaceutics, Marcel Dekker, Inc. 3rd Ed. (G. S. Banker & C. T. Rhodes, Eds.). The pharmaceutical compositions are formulated to contain suitable pharmaceutically acceptable carriers, and optionally can comprise excipients and auxiliaries that facilitate processing of the active compounds into preparations that can be used pharmaceutically. The mode of administration generally determines the nature of the carrier. The pharmaceutical compositions of the present invention can be manufactured using any conventional method, e.g., mixing, dissolving, granulating, dragee-making, levigating, emulsifying, encapsulating, entrapping, melt-spinning, spray-drying, or lyophilizing processes. An optimal pharmaceutical formulation can be determined by one of skill in the art depending on the route of administration and the desired dosage.

In certain embodiments, a compound of the present invention is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of formula (I) and (II) such that they do not adversely affect each other. Such compounds are suitably present in combination in amounts that are effective for the purpose intended. In one embodiment, a composition of this invention comprises a compound of formula (I) and (II), in combination with one or more chemotherapeutic agents used in "targeted therapy" and conventional chemotherapy, or therapeutic antibodies and antibody drug conjugates.

In a particular embodiment of anti-cancer therapy, a compound of this invention, or a stereoisomer, geometric isomer, tautomer, solvate, metabolite, isotopically-labeled derivate, pharmaceutically acceptable salt, or prodrug thereof, may be combined with other chemotherapeutic, hormonal or antibody agents, as well as combined with surgical therapy and radiotherapy. Combination therapies according to the present invention thus comprise the administration of at least one compound of formula (I) and (II), or a stereoisomer, geometric isomer, tautomer, solvate, metabolite, pharmaceutically acceptable salt, isotopically-labeled derivate, or prodrug thereof, and the use of at least one other cancer treatment method. The amounts of the compound(s) of the present invention and the other pharmaceutically active chemotherapeutic agent(s) and the relative timings of administration will be selected in order to achieve the desired combined therapeutic effect.

Non-limiting examples of suitable one or more additional therapeutic agents that can be combined with the PI3K inhibitors of the present invention are disclosed herein:

In one embodiment, the therapeutic agent is a tyrosine kinase inhibitor such as axitinib, bosutinib, dasatinib, crizotinib, erlotinib, gefitinib, ibrutinib, imatinib, lapatinib, nilotinib, ponatinib, ruxolitinib;

In one embodiment, the therapeutic agent is a MEK inhibitor such as selumetinib, PD0325901, trametinib, U0126-EtOH, PD184352, GDC-0623, BI-847325, cobimetinib, PD98059, BIX02189, binimetinib, pimasertib, SL327, BIX02188, AZD8330, TAK-733, honokiol, PD318088, refametinib;

In one embodiment, additional therapeutic agent is a BRAF inhibitor such as dabrafenib, vemurafenib;

In one embodiment, additional therapeutic agent is a BET (bromo and extra-terminal) inhibitor such as JQ1, I-BET-151, I-BET-762, OTX-015, TEN-010, CPI-203, CPI-0610, RVX-208;

In one embodiment, additional therapeutic agent is an autophagy inhibitor such as SP600125, U0126, 3-methyladenine, bafilomycin A1, chloroquine, SB202190, SB203580, LY294002, wortmannin;

In one embodiment, additional therapeutic agent is a PARP inhibitor such as iniparib, talazoparib, olaparib, rucaparib, veliparib, CEP 9722, MK 4827, BGB-290;

In one embodiment, additional therapeutic agent is a aromatase inhibitor such as aminoglutethimide, testolactone, arimidex, femara, aromasin, rivizor, lentaron, afema, 1,4,6-androstatriene-3,17-dione, 4-androstene-3,6,17-trione;

In one embodiment, additional therapeutic agent is a BCL-2 antagonist such as WEHI-539, ABT-737, TW-37, ABT-263, UMI-77, ABT-737, ABT-199, BDA-366, radotinib, obatoclax mesylate, HA14-1, Bax inhibitor peptide V5, sabutoclax, apogossypolone, BM-1074, marinopyrrole A, BAM7, Bax inhibitor peptide P5, Bax channel blocker, iMAC2, MIM1, muristerone A, 2,3-DCPE hydrochloride;

In one embodiment, additional therapeutic agents are a CDK4/CDK6 (and/or CDK9) inhibitor such as palbociclib, ribociclib, LY2835219, voruciclib, with or without an estrogen receptor modulator such as tamoxifen, toremifene, raloxifene, ospemifene, bazedoxifene, clomifene, lasofoxifene;

In one embodiment, additional therapeutic agent is an inhibitor of DNA synthesis and repair such as mitoxantrone, pixantrone, or cladribine;

In one embodiment, additional therapeutic agent is an immune checkpoint inhibitor such as pembrolizumab, nivolumab, ipilimumab, lambrolizumab, BMS-936559, MPDL3280A, and Medl-4736.

The combination therapy of the present invention may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Depending on the route of administration, a suitable dose can be calculated according to body weight, body surface area, or organ size. The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays used, as well as the pharmacokinetic data observed in human clinical trials.

The invention and the manner and process of making and using it, are now described in such full, clear, concise, and exact terms as to enable any person skilled in the art to which it pertains, to make and use the same. All publications and patent documents cited in this specification are incorporated herein by reference for all that they disclose.

What is claimed is:

1. A compound having the structure of formula (I):

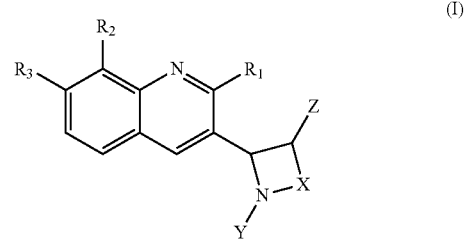

wherein:

X is selected from: —CH$_2$CH$_2$—, —CH=CHCH$_2$— or —CH$_2$CH$_2$CH$_2$—;

Z is hydrogen;

R$_1$ is selected from: phenyl, 2-pyridyl, 3-pyridyl, 4-pyridyl, piperidine, morpholine, or phenyl which is substituted by at least one substituent selected from: deuterium, —CH$_3$, —OCH$_3$, —OCF$_3$, or —F;

R$_2$ and R$_3$ are independently selected from: hydrogen, deuterium, C$_1$-C$_6$ alkyl, or halogen;

Y is selected from:

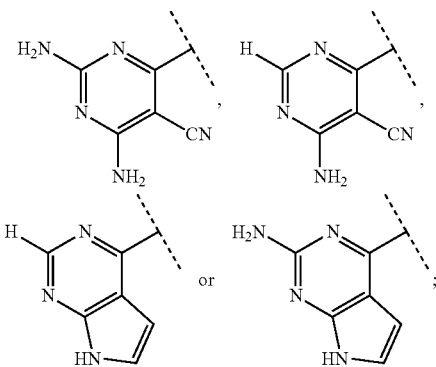

or a pharmaceutically acceptable salt thereof.

2. The compound or a pharmaceutically acceptable salt thereof according to claim 1, wherein R$_2$ and R$_3$ are independently selected from: hydrogen, deuterium, —F, —Cl, or —CH$_3$.

3. A compound having the structure of formula (II):

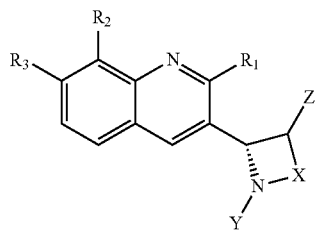

wherein:

X is —CH$_2$CH$_2$—;

Z is hydrogen;

R$_1$ is selected from: phenyl, pyridyl, or morpholine;

R$_2$ and R$_3$ are independently selected from: hydrogen, deuterium, —F, —Cl, or —CH$_3$;

Y is selected from:

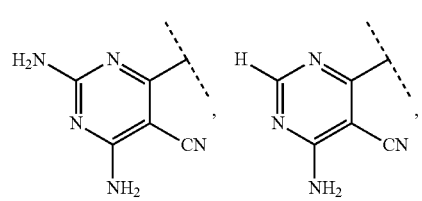

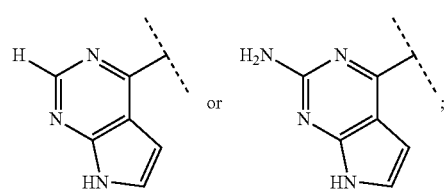

or a pharmaceutically acceptable salt thereof.

4. The compound of claims 1, 2 or 3, or a pharmaceutically acceptable salt thereof, wherein the compound is selected from:

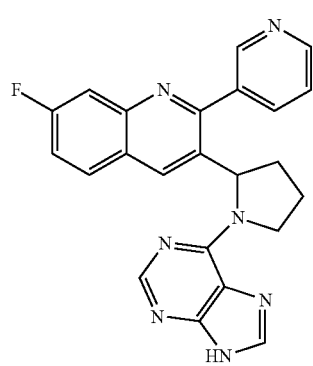

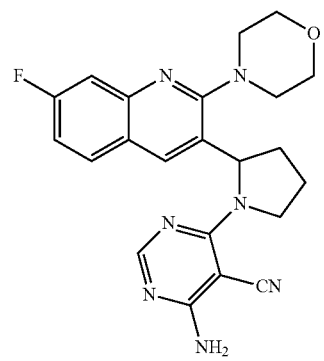

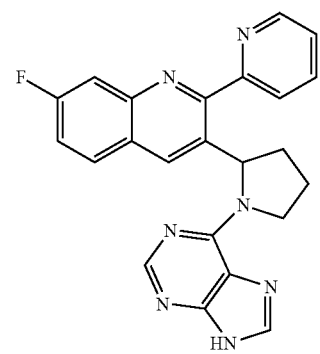

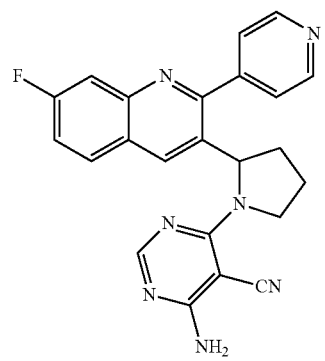

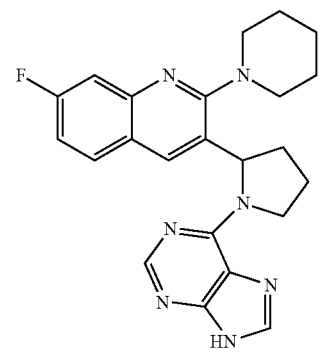

-continued
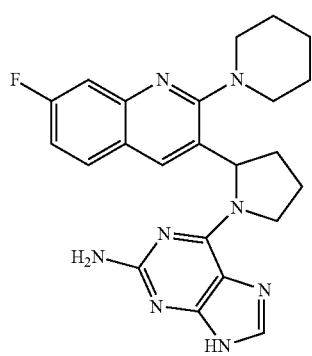
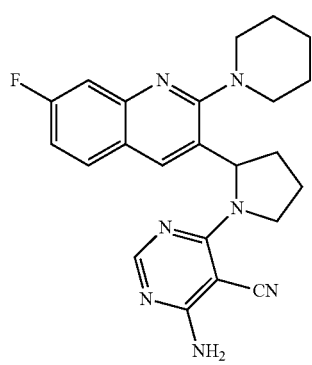
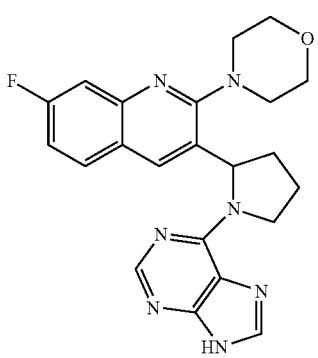
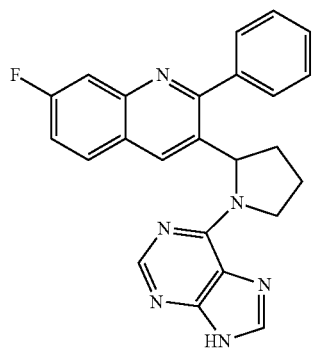
-continued
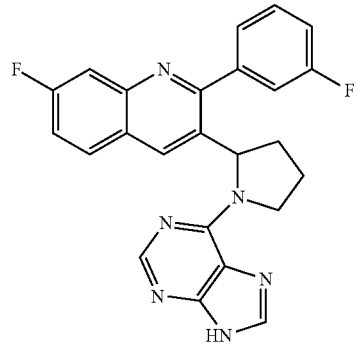
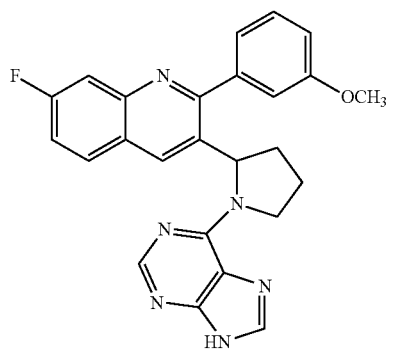
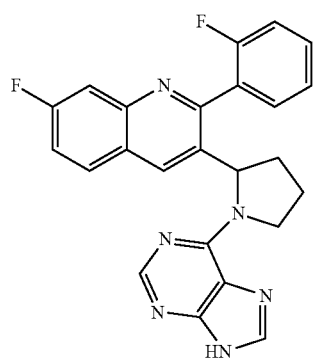
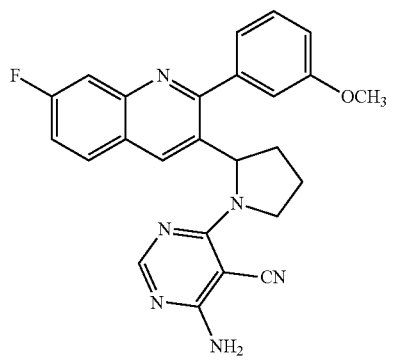

47
-continued
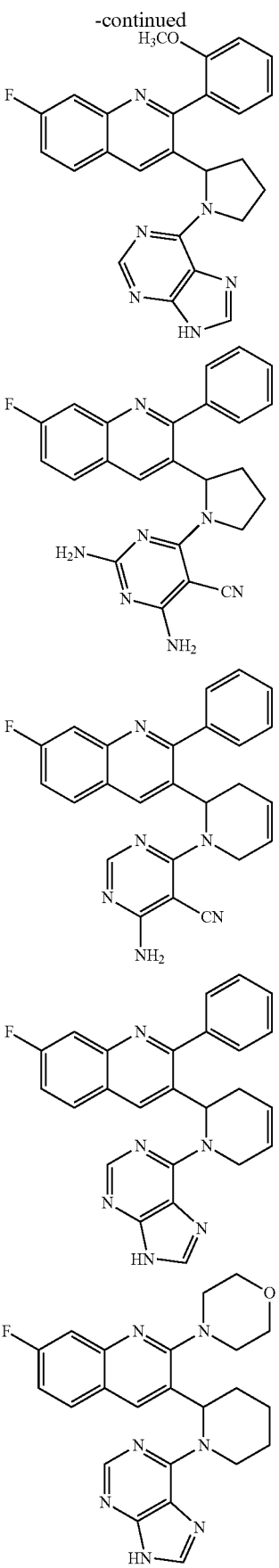
48
-continued
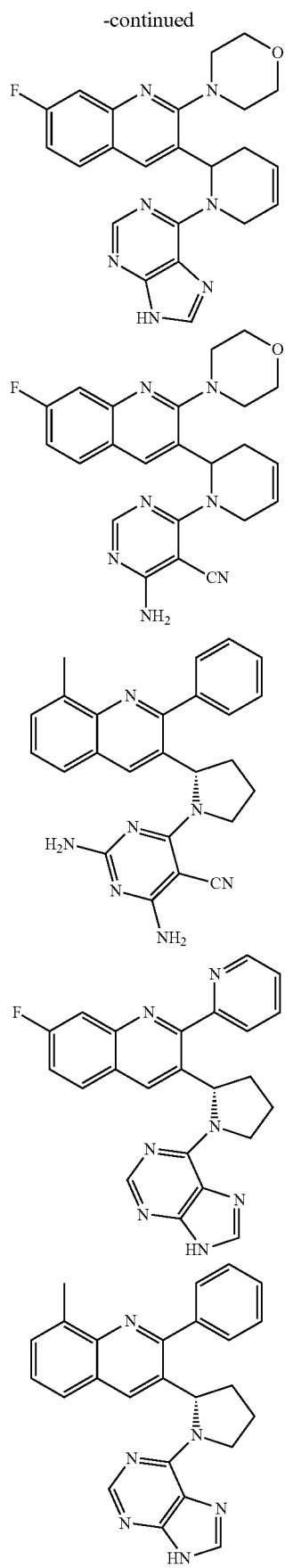

49
-continued
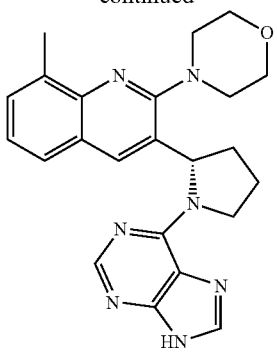
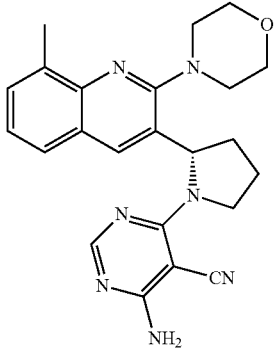
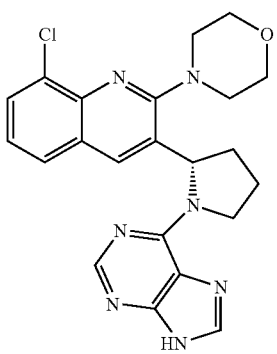
50
-continued
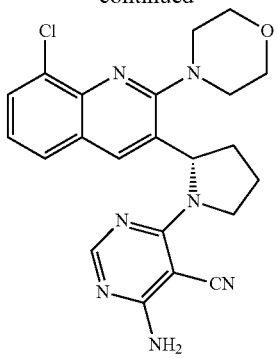
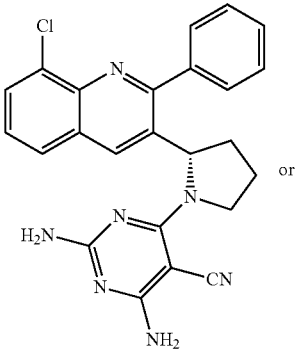
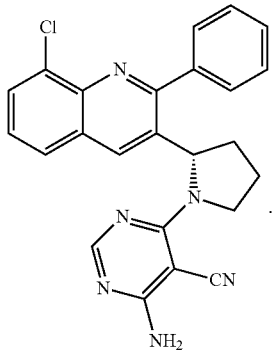 or
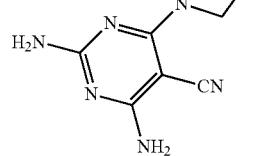.
* * * * *